(12) United States Patent
Zhang

(10) Patent No.: US 9,422,545 B2
(45) Date of Patent: Aug. 23, 2016

(54) LIPOPOLYSACCHARIDE-TARGETED PEPTIDE MIMIC VACCINE AGAINST Q FEVER

(71) Applicant: Guoquan Zhang,

| A | Chain | V-GENE | D-GENE | J-GENE | CDR3 length (pI) |
|---|---|---|---|---|---|
| | Heavy | IGHV13-2*02 (95.58%*) | IGHD1-1*01 | IGHJ4*01 (98.15%*) | 15 (4.4) |
| | Light | IGKV5-48*01 (95.34%*) | N/A | IGKJ2*01 (100.00%*) | 9 (13.0) |

```
                 ————PelB————
muScFv    MKYLLPTAAAGLLLLAAQPAMAECQLEESGGGLVRPGNSLKLSCVTS GFT
huScFv    ..................Q*..V......V.Q..R..R...AA. ...
           HCDR1         HFR2 loop          HCDR2
muScFv    FSNYRVH WLRQPPGKRLEWIA VIAVKSDNYGANYAESVKG RFTISRDDSK
huScFv    ........ .V..A...G...*                    ........N..
                                          HCDR3
muScFv    SSVYLQMNRLREEDTATYY CRSTVVVMGDYFAMDYW GQGTSVTVSSGGGG
huScFv    NTL.....S..A...V..                   ..............
           ——Linker——                                LCDR1
muScFv    SGGGGSGGGGSDIELTQSPAILSVSPGERVSFSC RASQNIGTYIH WYQQR
huScFv    ...........*V*.....F...T...K.TIT.                ....K
                         LCDR2
muScFv    TNGSPRLLIK YASESVS GIPSRFSGRGSGTDFTLSISSVESEDIADYY CQ
huScFv    PDQA.K....         .V.....S........FT...L.A..A.T..
           LCDR3                       —6xHis—
muScFv    QSNTWPYTF GGGTKLEIKRADAAPTVSKLAAALEHHHHHH
huScFv    .........
```

| | |
|---|---|
| m1E47 | SWF-HPQRRHSHQ |
| m1E415 | SWMPHPRVSPQH |
| m1E418 | M-HRAP S-THKL LP |
| m1E413 | ASW- HQHYMK-HKP |
| m1E411 | SEFI-HRHGDKEHK |
| m1E414 | QEFP-IRSWDMETN |
| m1E43 | SLTRHKPEPHRK |
| m1E41920 | SLTWHKHELHRK |
| m1E44 | SPPWHKHELHRK |
| m1E416 | GGWHKHI-SRSDP |
| m1E429 | YHKHP-HTYHNFK |
| m1E412 | HPKHP-HTHTNDQ |
| m1E410 | HMHM-HQHVAWTQ |
| m1E4817 | HMGMTKINYSAL |
| m1E41 | SNYSDVKRLPTV |
| m1E46 | SVNWQKQ-TISNL |

C. COMPETITIVE INHIBITION ELISA ANALYSIS OF BINDING ABILITY OF IMMUNE SERA FROM m1E41920-KLH –IMMUNIZED MICE WITH PI ANTIGEN.

LIPOPOLYSACCHARIDE-TARGETED PEPTIDE MIMIC VACCINE AGAINST Q FEVER

CROSS-REFERENCE TO RELATED APPLICATIONS

This application claims priority to U.S. Provisional Patent Application having Ser. No. 61/958,227, filed on Jul. 23, 2013, which is hereby incorporated by reference in its entirety.

GRANT STATEMENT

This invention was made with Government support under Grant No. RO1 AI083364 and Grant No. R21 AI75175 awarded by the National Institutes of Health. The Government has certain rights in the invention.

FIELD OF INVENTION

The present invention relates to a vaccine for preventing diseases related to natural and/or deliberate exposure to an intracellular Gram-negative bacterium, more specifically to a peptide mimic vaccine against Q fever.

SEQUENCE LISTING

A text file in compliance with ASCII and having a ".txt" extension has been electronically submitted via EFS-Web. The text file named "Sequence Listing" was created on Jul. 22, 2014, and is 7.74 KB. The text file is expressly incorporated by reference herein in its entirety.

BACKGROUND

*Coxiella burnetii* is a Gram-negative bacterium that causes acute and chronic Query fever (Q fever) in humans. Q fever can be asymptomatic or it can cause flu-like symptoms, such as high fever, chills, sweating, fatigue, muscle pain, headache, loss of appetite, nausea and vomiting. These acute symptoms can last one to two weeks. In chronic cases, infected persons can develop liver and heart disease and in some cases Q fever can be fatal. In these chronic cases, a small percentage of patients develop hepatitis or liver disease and jaundice. Another rare symptom is endocarditis, an inflammation of the lining of the heart cavity. Animals such as cattle, sheep and goats can carry *C. burnetii* in tissues involved in birth, such as the uterus, placenta, and birth fluids. Infected animals also release *C. burnetii* in milk and manure. Thus, people can acquire Q fever by inhaling infectious aerosols and contaminated dusts generated by animals or through animal products.

*C. burnetii* is an obligate intracellular Gram-negative bacterium that is an understudied category B select agent and can be transmitted via aerosol. The highly infectious nature of *C. burnetii* and its hardiness in adverse environmental conditions make this organism an important zoonotic pathogen, and potentially useful in bioterrorism and biological warfare. Since Q fever is a significant occupational hazard among veterinarians, meat processing plant workers, sheep and diary workers, livestock farmers, and researchers at facilities housing sheep, *C. burnetii* has been used for developing biological weapons in the past, and recently chronic Q fever cases have been increasing worldwide, Q fever is becoming a significant public health concern. Because *C. burnetii* infection can develop into more severe chronic diseases, vaccination is the logical approach to prevent individuals at risk of natural and deliberate exposure. Although formalin-inactivated *C. burnetii* phase I (PI) whole-cell vaccine provides near-complete protection in animal models as well as humans, it can induce severe local or systemic adverse reactions when administered to individuals with prior immunity to the agent. A formalin-inactivated whole cell vaccine, Q-vax, has been developed and widely used in high-risk individuals in Australia since 1989. Safe use of this vaccine requires screening of potential vaccines by skin test, serological tests, or in vitro lymphocyte proliferation assay. The time consuming and costly screening procedures limit the use of phase I vaccine (PIV) for a mass vaccination program. Currently, there is no licensed vaccine for preventing Q fever in the United States. Creation of a safe and effective new generation vaccine to prevent Q fever remains an important public health goal.

Based on prior studies, *C. burnetii* undergoes a lipopolysaccharide (LPS) phase variation in which its virulent smooth LPS phase I (PI) converts to an a virulent rough LPS phase II (PII) upon serial passage in eggs and tissue culture. It has been shown that PI vaccine (PIV) was more protective than PII vaccine (PIIV) in guinea pig and mouse models. An earlier study has shown that PI-LPS is able to elicit antibody (Ab) responses to PI and PII antigens and to confer protection against virulent *C. burnetii* challenge in a mouse model. One recent study also demonstrated that PI-LPS induced a level of protection similar to PIV, but PII-LPS did not provide measurable protection. Since cultivation of *C. burnetii* is difficult, hazardous, and requires the use of a BL3 facility, it is very difficult to generate large quantities of purified bacteria for isolation of LPS, which consequently limits the use of *C. burnetii* LPS to produce vaccines. Thus, a LPS-based Q fever vaccine has not been successful.

BRIEF SUMMARY

In one embodiment of the invention, a novel LPS-based vaccine and method of vaccination or conferring immunity against Q fever is described. The inventive vaccine comprises a polypeptide with a sequence of SLTWHKHELHRK (SEQ ID NO: 7) (m1E41920) or SPPWHKHELHRK (SEQ ID NO: 8) (m1E44), or at least 90% identity to m1E41920 or m1E44. According to one embodiment of the invention, the inventive vaccine against Q fever comprises a peptide m1E41920 conjugated to Keyhole limpet hemocyanin (KLH).

Other embodiments provide a method to identify and generate new vaccines to prevent diseases caused by intracellular Gram-negative bacteria. Methods based on peptide-mimic technology for identifying and generating new vaccines to prevent diseases caused by LPS-based intracellular Gram-negative bacteria are described. The method comprises the steps of identifying a protective monoclonal antibody specific to a LPS of a specific intracellular Gram-negative bacteria that causes the specific LPS-based intracellular Gram-negative bacterial infection in the subject; identifying one or more mimetic peptides by screening a Phage Display Library with the protective monoclonal antibody; and evaluating the one or more mimetic peptides to identify the one or more mimetic peptides that confer an effective protective antigen against the specific LPS-based intracellular Gram-negative bacterial infection in the subject.

Embodiments of the present invention provide methods and constructs for inhibiting, vaccinating and treating a *C. brunetti* infection. A PI-LPS specific monoclonal antibody 1E4 that was developed. The PI-LPS specific monoclonal antibody 1E4 is capable of inhibiting *C. burnetii* infection in mice. In another embodiment a mutant mouse antibody (muscFv1E4) and a mutant human antibody (huscFv1E4) were constructed and characterized. Both muscFv1E4 and huscFv1E4 were able to bind m1E41920 and live *C. burnetii*. Furthermore, muscFv1E4 and huscFv1E4 inhibits *C. burnetii* infection in mice and in mouse Bone Marrow-Derived Macrophages (BMDM) in vitro. Interestingly, huscFv1E4 inhibits *C. burnetii* infection in human macrophages in vitro. In one embodiment, humanized 1E4 (huscFv1E4) can be administered as a vaccine for preventing human Q fever.

BRIEF DESCRIPTION OF THE FIGURES

The patent or application file contains at least one drawing executed in color. Copies of this patent or patent application publication with color drawing(s) will be provided by the Office upon request and payment of the necessary fee.

Embodiments are described in detail below with reference to the attached drawing figures and pictures, wherein:

FIG. 5(A) represents the analysis of $V_H$ and $V_L$ gene usage and CDR sequence of 1E4.

FIG. 5(B) represents the analysis of $V_H$ and $V_L$ gene usage and CDR sequence of 1E4.

FIG. 6(A) compares the CDR amino acid sequence and structure of muscFv1E4 with huscFv1E4.

FIG. 8(A) illustrates the further identification of 1E4-specific phage clones.

DETAILED DESCRIPTION

*Coxiella burnetii* is a Gram-negative bacterium that causes acute and chronic Q fever in humans. Creation of a safe and effective new generation vaccine to prevent Q fever remains an important public health goal. Previous studies suggested that Ab-mediated immunity to *C. burnetii* phase I (PI-LPS) is protective. To identify the potential peptides that can mimic the protective epitopes on PI-LPS, a PI-LPS-specific mAb 1E4 was generated, characterized, and used to screen a phage display library. A mimetic peptide, m1E41920, inhibited *C. burnetii* infection in mice, suggesting that m1E41920 may specifically mimic the protective epitope of PI-LPS. Furthermore, 1E4 itself was able to inhibit *C. burnetii* infection in mice. To further understand the mechanisms of 1E4-mediated protection and to prove the feasibility of using 1E4 to prevent human Q fever, the Fab fragment of 1E4 (Fab1E4), recombinant murine single chain variable fragments (muscFv1E4) was examined and humanized single chain variable fragments (huscFv1E4) and found to retain the ability of 1E4 to inhibit *C. burnetii* infection. The results indicated that Fab1E4, muscFv1E4 and huscFv1E4 were able to inhibit *C. burnetii* infection in mice. Interestingly, treatment of *C. burnetii* with huscFv1E4 can significantly reduce *C. burnetii* infectivity in human macrophages.

A PI-LPS Specific Monoclonal Antibody 1E4

The *C. burnetii* stain used in these studies was *C. burnetii* Nine Mile phase I (PI) clone 7 (RSA493), which was propagated in L929 cells and purified by sucrose density centrifugation. Purified PI organisms were inactivated by 1% formaldehyde solution and used as whole cell antigen for ELISA. The protein concentration of inactivated PI whole cell antigen was measured by a Micro BCA™ (BiCinchoninic Acid) Protein Assay Kit (PIERCE, Rockford, Ill.).

Specific pathogen-free (SPF) 8 weeks old female BALB/c and SCID (CBySmn.CB17-Prkdc$^{scid}$/J) mice were purchased from the (JACKSON LABORATORY Bar Harbor, Me.). All mice were housed in sterile microisolator cages under SPF conditions in laboratory animal facility according to the Guide for the Care and Use of Laboratory Animals at the University of Missouri. The experimental protocols described in this report were approved by the Institutional Biosafety Committee and the Animal Care and Use Committee of University of Missouri (MU). All *C. burnetii* infection experiments were conducted in Animal Biohazard Safety Level 3 (ABL3) facilities at the MU Laboratory of Infectious Disease Research (LIDR).

One embodiment of the invention discloses a novel LPS-based vaccine against Q fever. The inventive LPS-based vaccine is safe, effective, and without inducing severe local or systemic adverse reactions when administered to a subject. A subject can be any animal, including mice, guinea pigs, chimpanzees, humans, and the like. To develop the LPS-based vaccine, the novel PI-LPS specific monoclonal antibody (mAb) 1E4 was identified.

Figure 1A:
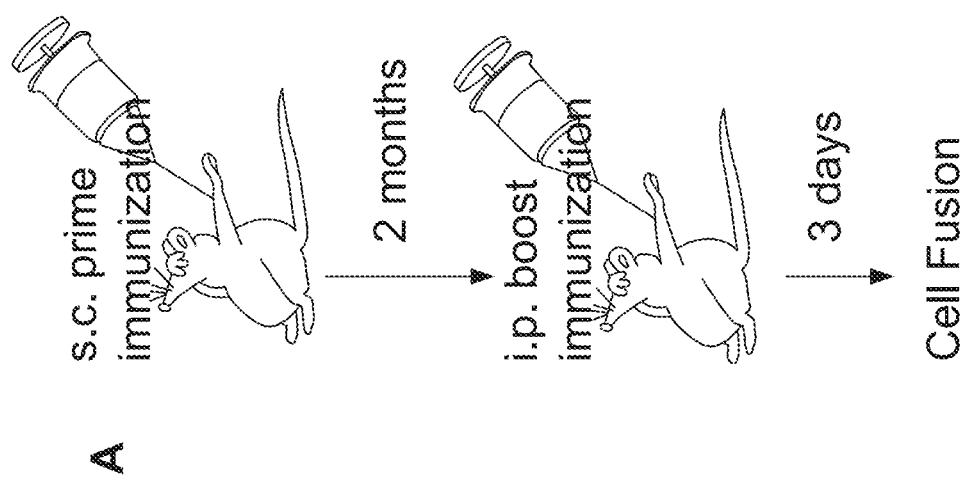
FIG. 1(A) illustrates the generation of the monoclonal antibody (mAb) 1E4.
Figure 1B:
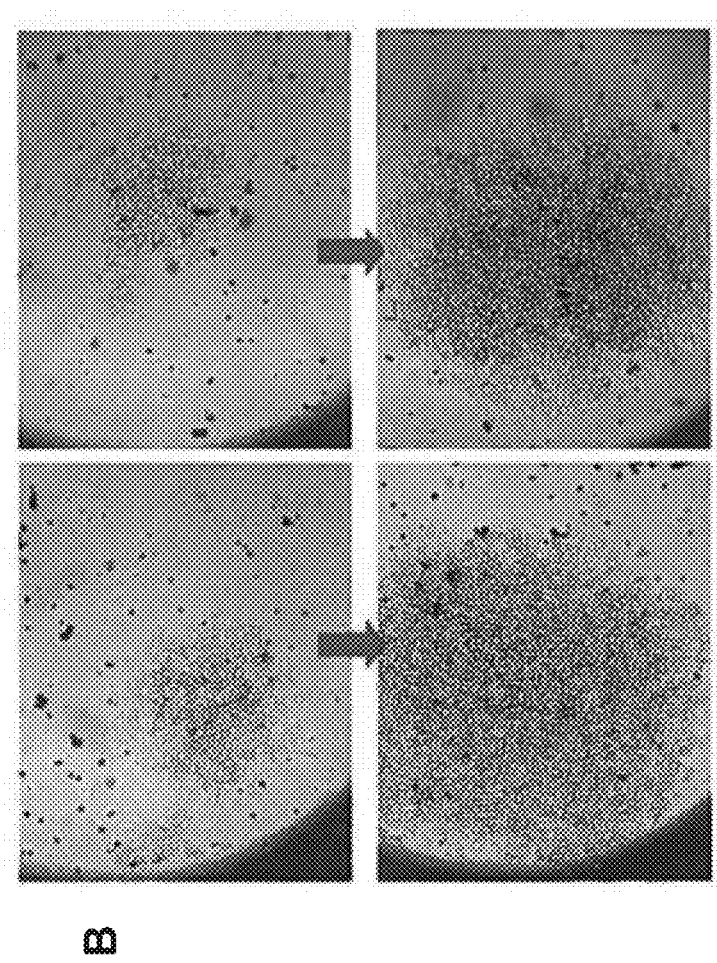
FIG. 1(B) illustrates the generation of the monoclonal antibody (mAb) 1E4.

Turning to FIGS. 1(A) and 1(B), to generate the monoclonal antibody (mAb) 1E4 against PI-LPS, 6-wk-old BALB/c mice were immunized with 10 μg formalin-inactivated *C. burnetii* NMI Ag four times at 3-wk intervals and used to isolate splenocytes. To develop monoclonal antibodies, the hybridomas were obtained from the fusion of splenocytes from PI-immunized BALB/c mice and SP2/0 myeloma cells, and then hybridoma supernatants were screened by ELISA for their ability to react with *C. burnetii* PI and PII antigens. FIG. 1(B) illustrates that ELISA-positive hybridoma cell populations were subcloned and cultured, whereas a total of 14 positive hybridomas were cloned. The positive hybridomas were cloned by limiting dilution and isotyped by ELISA. Cloned hybridomas were also analyzed by immunoblotting with proteinase K-treated and untreated PI and PII antigens.

One hybridoma, 1E4, which recognizes PI-LPS, was cultured in Hybridoma Serum Free Medium (INVITROGEN) and purified from the supernatants by using HiTrap protein G HP columns (GE HEALTHCARE) according to the protocol from manufacture. Purified 1E4 was desalted and concentrated by using an Amicon Ultra-15 centrifugal filter device with a 30 kDa molecular-weight cutoff (MILLIPORE). The purity of the purified 1E4 was analyzed by Coomassie blue-staining of SDS-PAGE gel and the protein concentration of 1E4 was measured by the Micro BCA™ (BiCinchoninic Acid) Protein Assay Kit.

Figure 2A:
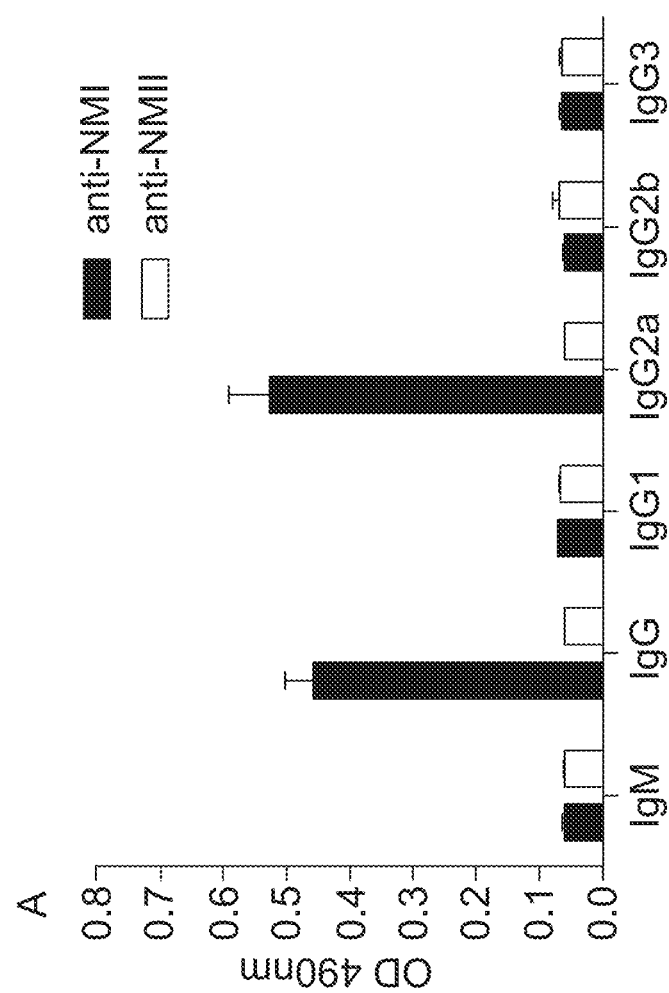
FIG. 2(A) illustrates the characterization of (mAb) 1E4 by ELISA and Western blotting.
Figure 2B:
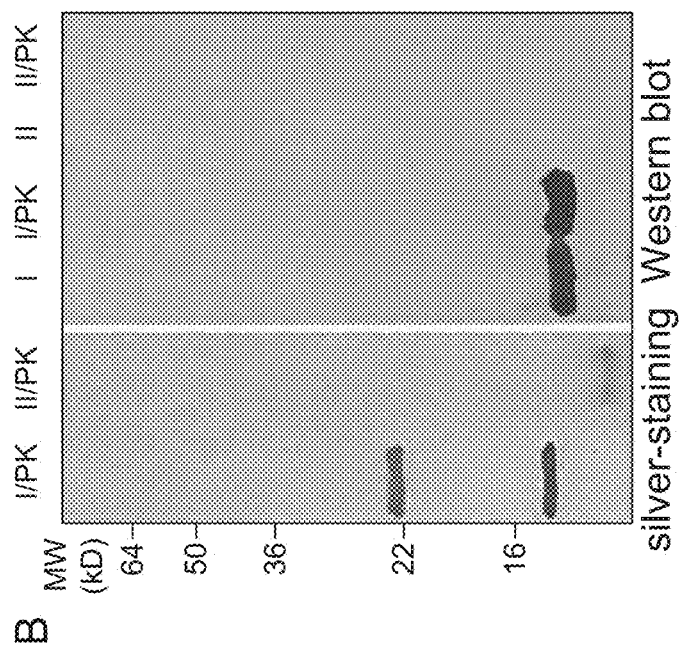
FIG. 2(B) illustrates the characterization of (mAb) 1E4 by ELISA and Western blotting.

Turning to FIGS. 2(A) and 2(B), illustrated is the characterization of (mAb) 1E4 by ELISA and Western blotting. As shown in FIG. 2(A), isotype of 1E4 by ELISA indicated that in PI antigen coated plate, 1E4 reacted with anti-IgG and -IgG2a secondary antibodies but did not react with anti-IgM, -IgG1, -IgG2b and -IgG3 secondary antibodies. This result suggests that the isotype of 1E4 is IgG2a. As shown in FIG. 2(B), Western blotting analysis demonstrated that 1E4 specifically reacted with a 14 kDa band in both PI and proteinase K digested PI antigens but did not react with PII, suggesting that 1E4 specifically recognizes epitopes on PI-LPS.

*C. burnetii* infection in mice does not cause death and clear clinical signs. However, infection can induce significant splenomegaly. Splenomegaly has been used as an indicator to monitor severity of *C. burnetii* infection in mice. In addition, because *C. burnetii* is difficult to grow on a plate and does not form clear plaques in cell culture, traditional methods cannot be used to measure the *C. burnetii* burden in animal tissues. Recently, a quantitative real-time PCR procedure has been developed and used to accurately measure the number of *C. burnetii* in the spleen. It was shown that splenomegaly is correlated with infection dose and also correlated with bacterial loading in the spleen, as measured by real-time PCR. This suggests that splenomegaly can be a useful indicator to monitor severity of infection and may be useful to evaluate the protective efficacy of vaccine. In this study, we used splenomegaly and bacterial burden and pathological changes in the spleen to evaluate the ability of 1E4 in inhibiting *C. burnetii* infection and the protective efficacy of mimic peptide vaccine-induced protection against *C. burnetii* challenge in BALB/c mice. The results provided additional evidence to support that mouse splenomegaly sublethal challenge model can be used to measure the ability of Ab-mediated protection and the protective efficacy of vaccine candidates against *C. burnetii* infection. In addition, our results suggest that pathological change in the spleen can be used as an additional indicator to evaluate the ability of Ab-mediated protection and the protective efficacy of vaccines against *C. burnetii* infection.

Figure 3A:
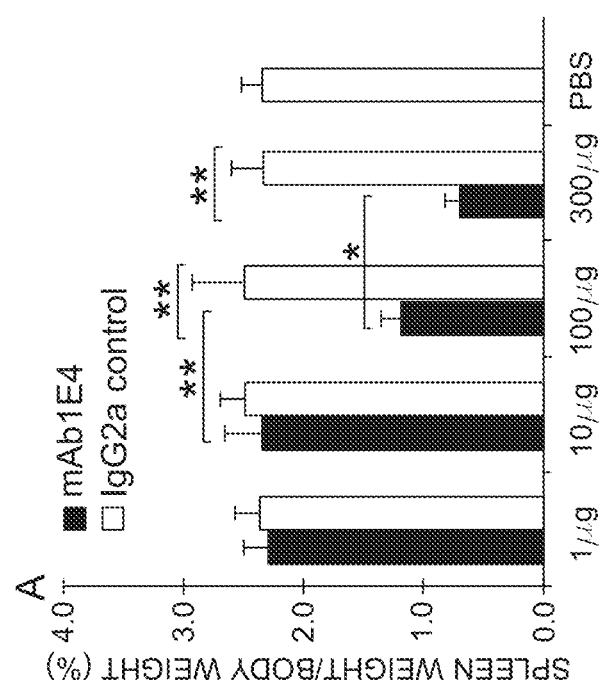
FIG. 3(A) evaluates the ability of 1E4 to inhibit *C. burnetii* infection in vivo.
Figure 3B:
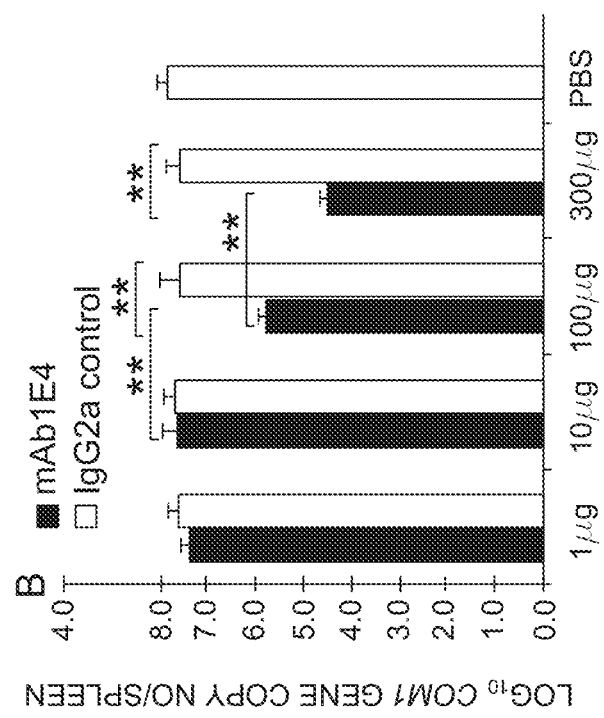
FIG. 3(B) evaluates the ability of 1E4 to inhibit *C. burnetii* infection in vivo.
Figure 3C:
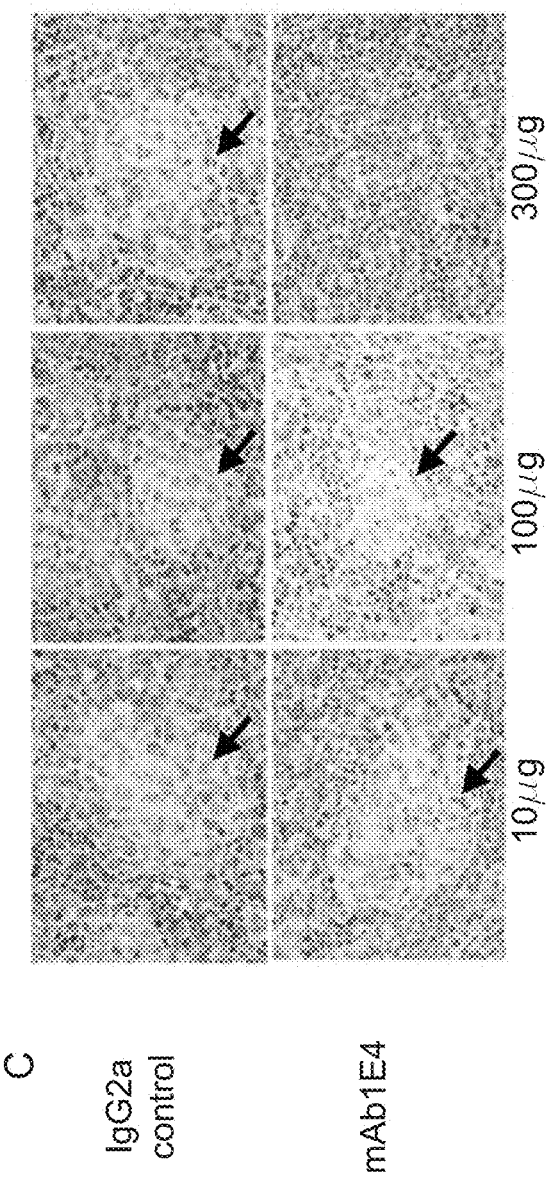
FIG. 3(C) evaluates the ability of 1E4 to inhibit *C. burnetii* infection in vivo.

In one embodiment, with reference to FIGS. 3(A) and (B) it was demonstrated that a PI-LPS specific monoclonal antibody (mAb) 1E4 was able to inhibit *C. burnetii* infection in vivo; passive transfer of 1E4 was able to confer significant protection against Q fever in mice. FIGS. 3(A) and 3(B) show the ability of 1E4 to inhibit *C. burnetii* infection in vivo. The inhibition of *C. burnetii* was performed by incubation of $1 \times 10^7$ virulent *C. burnetii* NMI with 1, 10, 100 and 300 μg of purified 1E4, or mouse IgG2a isotype control at 4° C. overnight. Splenomegaly and bacterial burden in the spleen were measured at 14 days post infection and used as indicators to evaluate the ability of 1E4 to inhibit *C. burnetii* infection in BALB/c mice. Compared to mice infected with PBS or mouse IgG2a isotype control-treated *C. burnetii*, 1E4 was able to inhibit *C. burnetii* infection in a dose-dependent manner. The splenomegaly analysis is included in the FIG. 3(A) plot, while the real-time-PCR analysis is in FIG. 3(B), and both analyses demonstrate that 1E4 is a protective mAb. For both FIGS. 3(A) and 3(B), *p<0.05 and **p<0.01. The mAb 1E4 was able to inhibit *C. burnetii* infection in vivo in a dose-dependent manner, suggesting that 1E4 may directly neutralize or become bactericidal toward *C. burnetii* to block *C. burnetii* infection. FIG. 3(C) shows pathological changes in the spleen of mice infected with IgG2a isotype control, 10, 100, or 300 µg 1E4-treated *C. burnetii*. Robust extramedullary hematopoiesis and increased macrophages with more aggregates occurred in mice infected with PBS, IgG2a isotype control, or lower doses (1 or 10 µg) of 1E4-treated *C. burnetii*, whereas there were decreased extramedullary hematopoiesis and few to no aggregates of macrophages in mice infected with 100 or 300 µg 1E4-treated *C. burnetii*. In addition, multifocal moderate to large accumulations of macrophages (arrow) were present throughout red pulp of spleens of mice infected with PBS, IgG2a isotype control, or lower doses (1 or 10 µg) of 1E4-treated *C. burnetii*. In contrast, multifocal accumulations of macrophages (arrow) were fewer and smaller in red pulp of spleens of mice infected with 100 µg of 1E4-treated *C. burnetii*. In the spleen of mice infected with 300 µg 1E4-treated *C. burnetii*, there were only two small accumulations of macrophages present in red pulp of spleen of one of four mice. Thus, pathological changes in the spleen correlated to splenomegaly and bacterial burden in the spleen. These results demonstrate that 1E4 was able to inhibit *C. burnetii* infection in vivo in a dose-dependent manner, suggesting that 1E4 may directly neutralize or become bactericidal toward *C. burnetii* to block *C. burnetii* infection. FIG. 3(C) shows pathological changes in the spleen at 14 days postchallenge. The data presented in each group are the average with SD of four mice. Original magnification ×410.

It was shown that both passive transfer of immune sera or Abs and premixed immune sera or Abs with *C. burnetii* were able to transfer significant protection to naive recipient mice. Although the mechanisms of Ab-mediated protection against *C. burnetii* infection remain unclear, the Ab binding with bacteria is necessary for direct bactericide, neutralization, or opsonization. To reduce the influence of unpredictable factors in in vivo variables, such as Ig biodistribution and catabolism on the Ab-pathogen complex formation, immune sera, mAb were premixed with *C. burnetii* for evaluating its ability to inhibit *C. burnetii* infection in this study. In addition, premixing immune sera or mAb with *C. burnetii* may be able to provide quantitative measurement of their ability to inhibit *C. burnetii* infection.

Figure 4A:
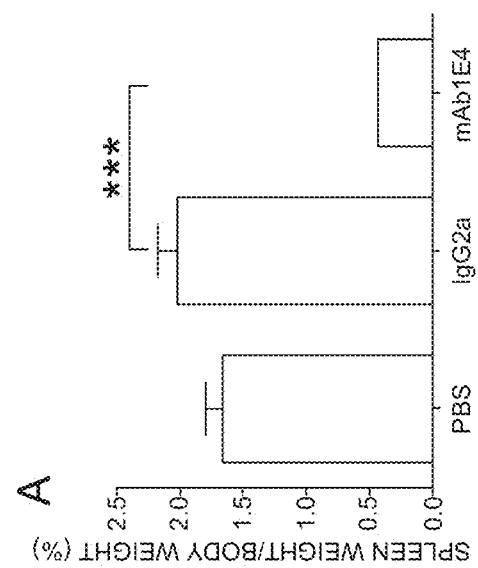
FIG. 4(A) evaluates the ability of 1E4 to confer protection in mice against *C. burnetii* aerosol infection.
Figure 4B:
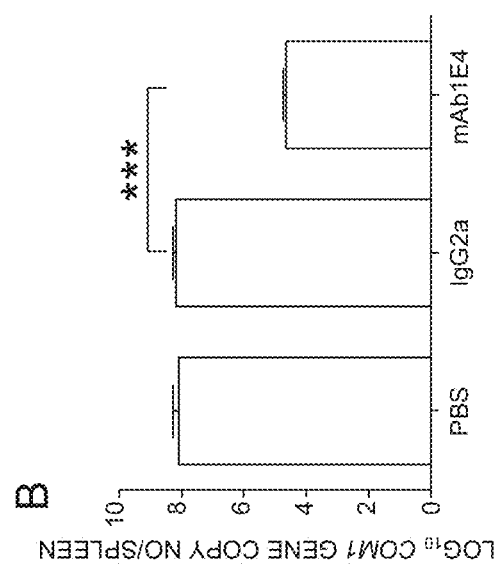
FIG. 4(B) evaluates the ability of 1E4 to confer protection in mice against *C. burnetii* aerosol infection.
Figure 4C:
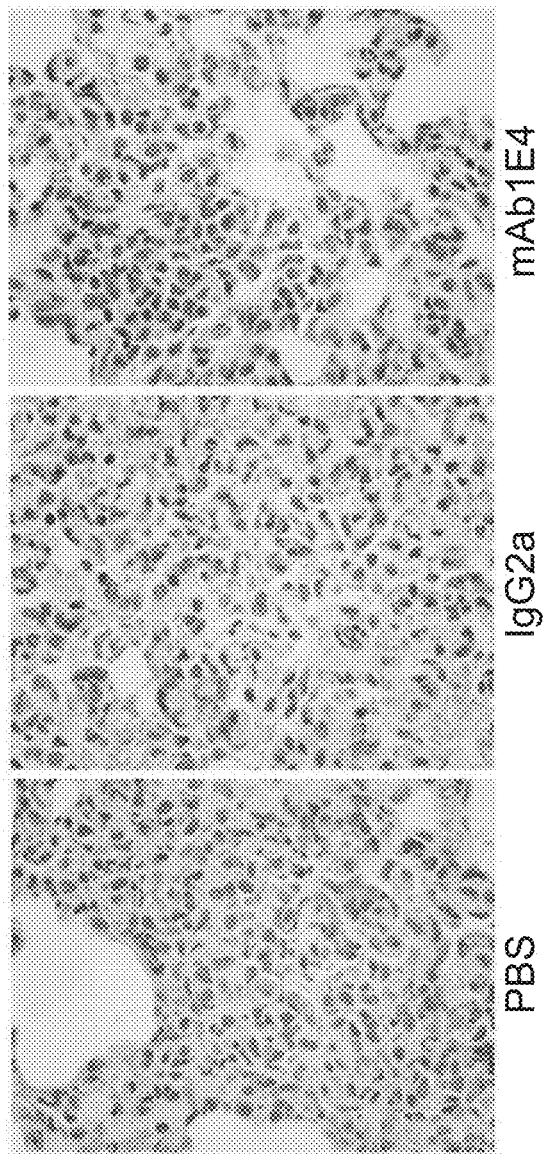
FIG. 4(C) evaluates the ability of 1E4 to confer protection in mice against *C. burnetii* aerosol infection.
Figure 4D:
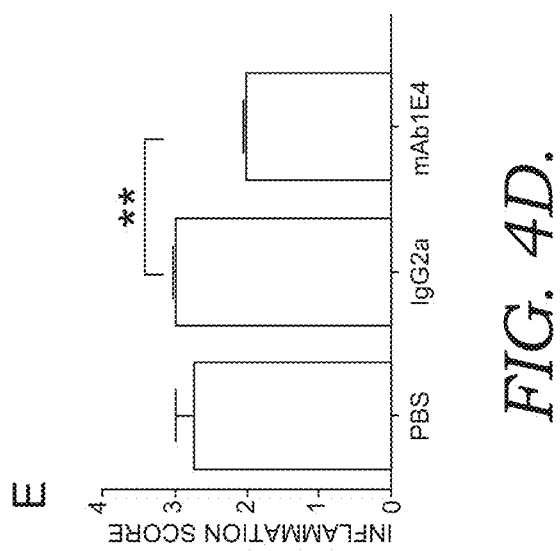
FIG. 4(D) evaluates the ability of 1E4 to confer protection in mice against *C. burnetii* aerosol infection.
Figure 4E:
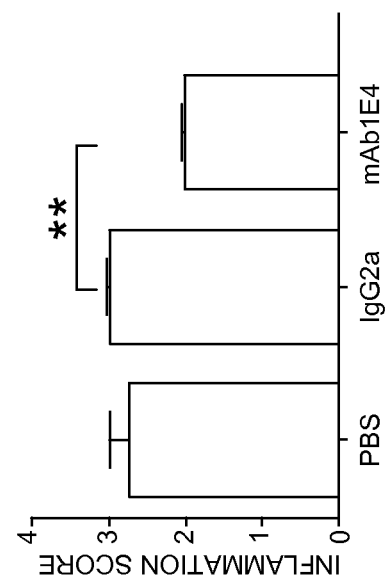
FIG. 4(E) evaluates the ability of 1E4 to confer protection in mice against *C. burnetii* aerosol infection.

As shown in FIG. 4A, to determine whether passive transfer of Abs can provide protection against *C. burnetii* natural infection, we examined if passive transfer of 1E4 would provide significant protection against *C. burnetii* aerosol challenge in SCID mice, compared to mice receiving PBS or mouse IgG2a isotype control, splenomegaly was significantly reduced in mice receiving 1E4 (p<0.001). In FIG. 4A, as compared to PBS or mouse IgG2a isotype control recipient mice, significantly lower *C. burnetii* genome copies were detected in spleens and lungs from 1E4 recipient mice (p<0.001, FIGS. 4(B) & (C)). In addition, differences in interstitial inflammation as measured by the concentration of macrophages and neutrophils in interalveolar septum and alveolar spaces were observed in the lungs between PBS or IgG2a and 1E4 receiving mice (FIG. 4(D)). Moderate to large accumulations of macrophages and neutrophils were observed in the lungs from PBS or IgG2a receiving mice, which affected more than 10% of lung parenchyma. In contrast, few small scattered accumulations of neutrophils and macrophages of mild to moderate accumulations of macrophages and neutrophils were present in the lungs from mice receiving 1E4, which affected less than 10% of lung parenchyma. The severity of inflammation in the lung was significantly reduced in 1E4 receiving mice as compared with PBS or IgG2a receiving mice (p<0.01, FIG. 4E). These observations indicated that passive transfer of 1E4 provided protection against aerosolized *C. burnetii* challenge-induced inflammatory response in the lung.

These results also demonstrated that passive transfer of PI-LPS specific mAb 1E4 was able to confer significant protection against aerosolized *C. burnetii* in naïve recipient mice, suggesting that the *C. burnetii* aerosol infection mouse model can be used to evaluate the efficacy of Ab-mediated protection against *C. burnetii* natural infection. Passive immunization of 1E4 was performed by i.p. injection of 300 µg of purified 1E4 into each SCID mouse. In addition, SCID mice receiving 300 µg of control IgG2a or PBS were used as negative controls. All mice were exposed to virulent PI using a Liquid Sparging Areosolizer. This apparatus ensures a uniform dose of bacteria to the lower airways though a nose-only aerosol exposure. A total of $1\times10^9$ bacteria resuspended in 5 ml of PBS was aerosolized and used to challenge SCID mice. The total exposure time was approximately 30 minutes. Samples collected from bubbling the aerosol through PBS showed that of the $1\times10^9$ starting concentration, each mouse actually received approximately $1\times10^7$ *C. burnetii*. Mice were sacrificed at 14 days post infection. Mouse body and spleen weights were measured, and a portion of lung and spleen from each mouse was collected for real-time-PCR analysis. The ability of 1E4 to confer protection against *C. burnetii* aerosol infection was evaluated by comparing splenomegaly, bacterial burden and histopathological changes in the lung and spleen at 14 days post infection with controls.

TABLE 1

| Primer | Sequence |
| --- | --- |
| FVLk (SEQ. ID No. 29) | 5'-gac att gag ctc acc cag tct cca-3' |
| RCLk (SEQ. ID No. 30) | 5'-ggc tcg agg aag atg gat aca gtt ggt gca-3' |
| FVH1 (SEQ. ID No. 31) | 5'-ag gtg cag ctc gag gag tca gga cc-3' |
| FVH2 (SEQ. ID No. 32) | 5'-gag gct cag ctc gag cag tct gga cc-3' |
| FVH3 (SEQ. ID No. 33) | 5'-cag gtc caa ctc gag cag cct ggg gc-3' |
| FVH4 (SEQ. ID No. 34) | 5'-gag gtt cag ctc gag cag tct ggg gc-3' |

TABLE 1-continued

| Primer | Sequence |
|---|---|
| FVH5 (SEQ. ID No. 35) | 5'-gag gtg aag ctc gag gaa tct gga gg-3' |
| FVH6 (SEQ. ID No. 36) | 5'-gag gta aag ctc gag gag tct gga gg-3' |
| FVH7 (SEQ. ID No. 37) | 5'-gaa tgt cag ctc gag gag tct ggg gg-3' |
| FVH8 (SEQ. ID No. 38) | 5'-gag gtt cag ctc gag cag tct gga gc-3' |
| RCHg2a (SEQ. ID No. 39) | 5'-gtt ctg act agt ggg cac tct ggg ctc-3' |

The 1E4 has Unique $V_H$ and $V_L$ Gene Usage and CDR Sequence

Figure 5B:
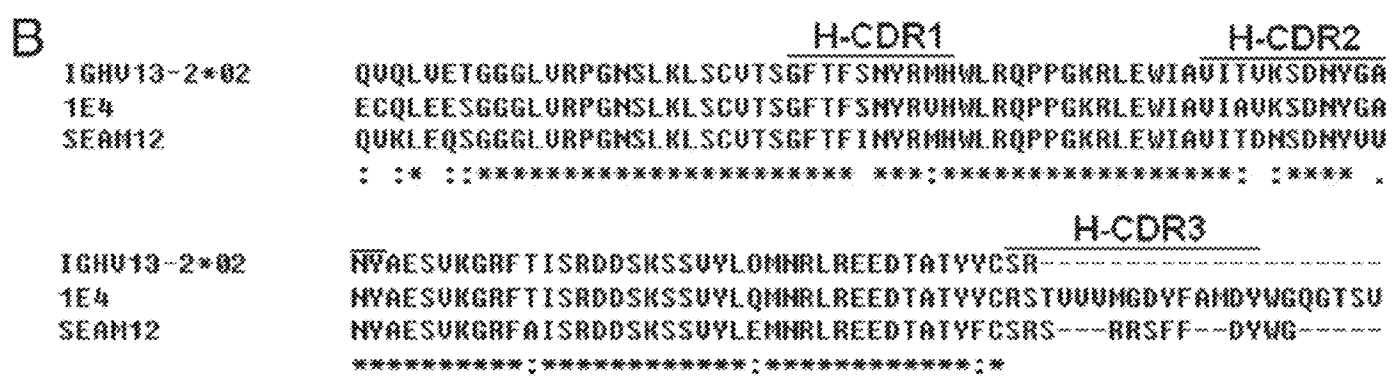
Figure 5C:
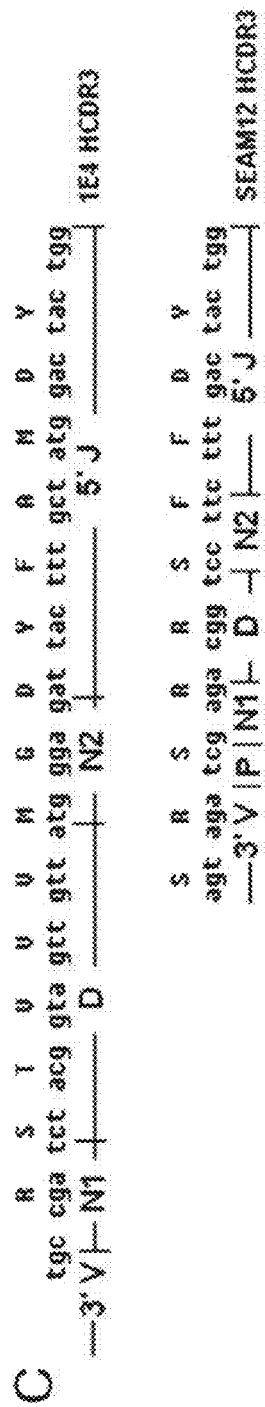
FIG. 5(C) represents the analysis of $V_H$ and $V_L$ gene usage and CDR sequence of 1E4.

The 1E4 $V_H$ gene was only amplified by using FVH7-RCHg2a primer pairs (data not shown). As shown in FIG. 5(A), the IMGT/V-QUEST analysis of 1E4 nucleotide sequences {GenBank accession numbers: JX139949 ($V_H$ gene) and JX139950 ($V_L$ gene)} and indicate that the 1E4 $V_H$ gene is encoded by a rarely reported murine germline family IGHV13-2. BLAST search of the 1E4 $V_H$ gene nucleotide and amino acid sequences in the GenBank non-redundant sequence databases found that only one reported bacterial carbohydrate antigen specific antibody, the anti-*Neisseria meningitidis* group B polysaccharide mAb SEAM12 (GenBank: DQ113493.1), was derived from IGHV13-2. FIG. 5(B) shows the alignment analysis of respective amino acid sequences of 1E4, IGHV13-2 and SEAM12 $V_H$ gene. Compared to the germline gene IGHV13-2, several mutations were identified in HCDR1 and HCDR2 regions of 1E4 and SEAM12 $V_H$ genes. Interestingly, the HCDR3 region differed in length, pI and hydrophobicity between 1E4 and SEAM12 (FIGS. 5(B) and (C)). The HCDR3 of 1E4 has 15 amino acids but there are only 10 amino acids found in the HCDR3 of SEAM12. The HCDR3 of 1E4 has a much lower pI (4.4) than the HCDR3 of SEAM12 (pI 10.75). 1E4 contains three highly hydrophobic valine amino acids and the average normalized Kyte-Doolittle hydrophobicity of HCDR3 loop is greater than 1.12. In contrast, the SEAM12 HCDR3 contains three highly charged arginine amino acids and the average hydrophobicity is just −1.29. FIG. 5: Panel A, analysis of 1E4 $V_H$ and $V_L$ gene usage by IMGT/V-QUEST. a: identity to germline genes. Panel B, comparison of amino acid sequence of 1E4 $V_H$ gene with the anti-*Neisseria meningitidis* group B polysaccharide mAb SEAM12 and murine germline family IGHV13-2 by ClustalW program. A star (*) indicates the same amino acid residue identity in a position, while a dot (:) indicates a different residue, and a dash (-) indicates inserted spaces placed in the sequence to provide maximum identity. Panel C, comparison of the HCDR3 conjunction between 1E4 and SEAM12. N: nucleotide addition mutation; P: P deletion mutation.

Characterization of a Mutant Mouse Antibody (muscFv1E4) and a Mutant Human Antibody (huscFv1E4)

Figure 6B:
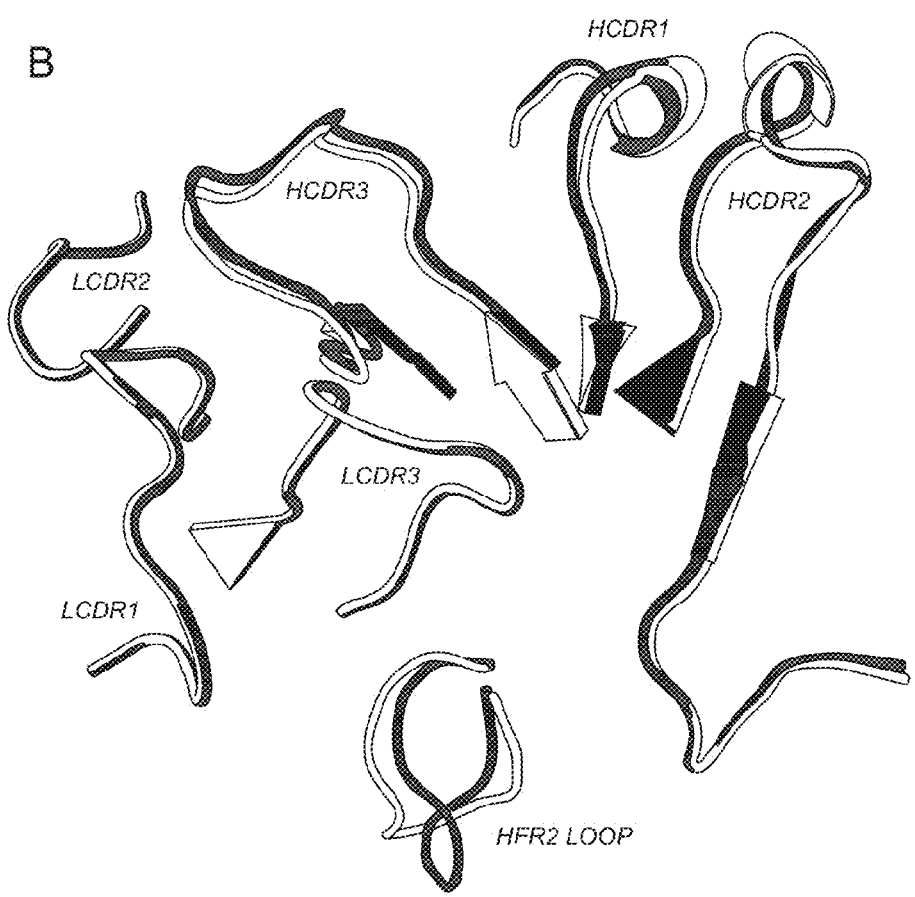
FIG. 6(B) compares the CDR amino acid sequence and structure of muscFv1E4 with huscFv1E4.

The Complementarity Determining Regions (CDRs) in the variable regions of Abs play a critical role in their specificity and affinity by means of shape and charge complementarities. To define the role of CDRs in the Fab fragment of 1E4, a mutant mouse antibody (muscFv1E4) and a mutant human antibody (huscFv1E4) were designed and constructed by humanized CDR grafting (FIG. 6A). The structure models of the muscFv1E4 and huscFv1E4 were superimposed to determine conformational changes in the loop regions. As depicted in FIG. 5B, the muscFv1E4 CDR colored in black showed nearly identical loop structures compared to the huscFv1E4 CDRs colored in gray. The root mean square (RMS) which can be used to measure the three dimensional structural similarity was calculated by SwissPdb Viewer. Higher RMS values usually mean greater conformational dissimilarity and 1.5 A° was defined as the Ab similarity cut-off values. The RMS of the CDR loops in muscFv1E4 and huscFv1E4 structural alignment model ranged from 0.2 to 1.0 A° indicating a significantly similar conformation. However, as shown in FIG. 6B, an apparent difference between muscFv1E4 and huscFv1E4 was observed in the heavy changes FR2 (HFR2) loop. SwissPdb Viewer calculation showed conformational changes at PPGKR residues of HFR2, resulting in a very high average RMS value of 2.88 A°. These results indicate that except for CDR domains, huscFv1E4 has less than 70% sequence identity to its parent mAb 1E4 as well as a significant conformational change in the HFR2 region, suggesting that the muscFv1E4 derived mutation construction, huscFv1E4, may be useful for identifying the role of CDRs in the Fab fragment of 1E4. To purify the 1E4 and Fab fragment of 1E4, hybridoma 1E4 was cultured in Hybridoma Serum Free Medium (INVITROGEN, Grand Island, N.Y.) and 1E4 was purified from the supernatants using protein G columns. The Fab fragment of 1E4 was generated by papain digestion of 1E4 with an ImmunoPure Fab Preparation Kit (THERMO FISHER SCIENTIFIC, Rockford, Ill.) and separated from undigested 1E4 and the constant domain fragment (Fc) by using Protein A column. The flow through fraction was collected as the purified Fab fragment of 1E4. The purity of purified 1E4 and the Fab fragment were analyzed by SDS-PAGE and Western blotting. The concentrations of 1E4 and the Fab fragment were measured by Bradford assay (BIO-RAD, Hercules, Calif.).

To generate muscFv1E4 of 1E4, total RNA was extracted from ~$10^5$ monoclonal 1E4 hybridoma cells using QIAgen RNeasy Mini Kit (QIAGEN, Valencia, Calif., USA) and the cDNA was obtained using QuantiTectRev Transcription Kit (QIAGEN) according to the manufacturer's instructions. The variable heavy chain (VH) and variable light chain (VL) genes were amplified separately by PCR. The PCR products of VL and VH genes were gel purified using QIAquick gel extraction kit (QIAGEN) and separately cloned into pCR2.1-TOPO vector (INVITROGEN). Randomly selected clones were sequenced using the M13 primers at the MU's DNA core facility. The sequences of VL and VH genes were compared with 1E4 nucleotide sequences in the Genbank (VL gene: JX139950 and VH gene: JX139949), respectively. The correct 1E4 VH and VL genes were designated as pTVHE4 and pTVLE4, respectively, and used as PCR templates to amplify full-length 1E4 scFv gene. Primers were designed to introduce Nde I restriction sites and the pelB leader sequence, respectively. One primer was designed to introduce the Hind III restriction sites. Primers were designed to carry overlapping sequences encoding the link peptide $(Gly_4Ser)_3$. The amplified full-length scFv gene was subcloned into the Nde I/Hind III site of pET23a via overlap extension (SOE) methods (EMD MILLIPORE, Darmstadt, Germany). The correct clone was selected based on DNA sequencing and used as the recombinant plasmid pETmuscFv1E4, in which the C-terminal domain of scFv was fused with a His-tag for improved purification and immune identification.

The construction of a humanized 1E4 scFv (huscFv1E4) by human complementarity determining region (CDR)-grafting was established as follows: the VH and VK sequences of 1E4 (GenBank: JX139949 and GenBank: JX139950) were compared with the human VH and VK gene families using NCBI IgBLAST tools. The human V genes frameworks IGHV3-30-3*01 (71% identical to 1E4 VH framework) and IGKV6D-41*01 (66% identical to 1E4 VL framework) were chosen to accept the 1E4 CDRs based on their highest amino acid sequence identity. Almost all of the framework amino acid residues that are different between 1E4 and human sequences were changed to human sequences. Four murine residues, including VH2, VH48, VL2, and VL4, which belong to the "vernier zone" were retained at their positions as "back mutation", because these residues may strongly affect the structure of CDRs and the antibody affinity. The designed Nde I/Hind III flanked humanized 1E4 scFv DNA sequence (the N terminus pelB leader sequence upstream from the humanized 1E4 VH chain-the $(Gly_4Ser)_3$ peptide linker-the humanized 1E4 VL chain) was synthesized by (GENSCRIPT CORPORATION Scotch Plaines, N.J., USA) and cloned into pUC57 vector, resulting in pUChuscFv1E4. The Nde 1/Hind III fragment of pUChuscFv1E4 was then cloned into pET23a to generate the expression plasmid pEThuscFv1E4.

The automatic modeling of variable regions of muscFv1E4 and huscFv1E4 were established by canonical structure method. The deduced VH and VL amino acid sequences of muscFv1E4 and huscFv1E4 were submitted to the Prediction of ImmunoGlobulin Structure (PIGS), respectively. The resulting models were aligned and displayed by PyMOL (DELANO SCIENTIFIC, San Carlos, Calif.). In addition, the muscFv1E4 and huscFv1E4 models were superimposed by DeepView v4.1 to calculate the root mean square (RMS) for comparing their three dimensional structural similarity.

Identification of PI-LPS Mimetic Peptides

Figure 7:
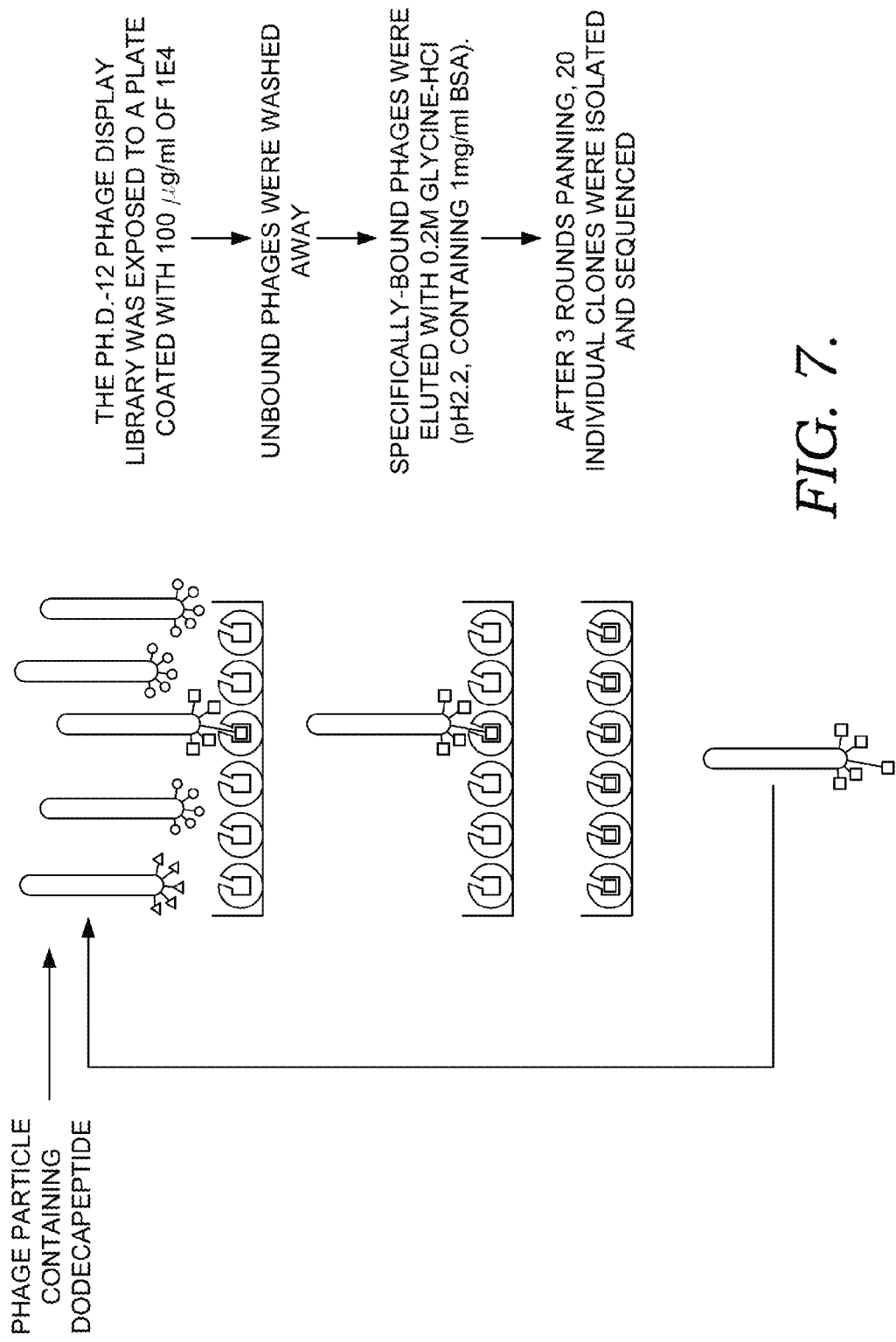
FIG. 7 illustrates the procedure for identifying the peptides via screening.

In one embodiment, peptide-mimic technology was employed for identifying peptide mimics on PI-LPS by screening a Phage Display Library with mAb 1E4. Refer to FIG. 7, which illustrates the procedure for identifying the peptides via screening. To identify the peptides that can mimic the protective epitopes of PI-LPS, the Ph.D.-12 Phage Display Peptide Library (NEW ENGLAND BIOLABS INC., Beverly, Mass.) was screened with 1E4 in a solid-phase support system. Three subsequent biopanning rounds were carried out according to the manufacturer's instructions. Briefly, 100, 10, and 1 μg/ml of 1E4 were used in the first, second and third round panning, respectively. Amplified phage clones were purified by precipitating the phage particles with PEG/NaCl (20% polyethylene glycol 8000 and 2.5 M NaCl). The selected phage DNAs were extracted by using iodide buffer (10 mM Tris-HCl [pH 8], 1 mM EDTA, 4 M NaI) according to the manufacturer's instructions. Sequence analysis of the peptide inserts was performed by automated dideoxyoligonucleotide sequencing using the −96 M13 primer (NEW ENGLAND BIOLABS INC., at the MU's DNA core facility. The inserted peptide sequences were deduced from the DNA sequences. A total of 20 phage plaques were randomly picked, amplified and sequenced.

Figure 8B:
FIG. 8(B) illustrates the further identification of 1E4-specific phage clones.

The 20 phage plaques were further analyzed to identify the 1E4-specific phage clones: m1E41920 and m1E44 with the sequence, SLTWHKHELHRK (SEQ ID NO: 7) and SPP-WHKHELHRK (SEQ ID NO: 8), respectively. Turning to FIGS. 8(A) and 8(B), illustrated is the further identification of 1E4-specific phage clones. As shown in amino acid sequence alignment analysis (FIG. 8(A)), m1E41920 and m1E44 have the closest alignment. A total of 16 mimetic peptides (with unique sequences) that could bind to 1E4 were identified after three rounds of biopanning against 1E4. As shown in FIG. 8(B), Each of the sequenced unique phage clones was analyzed by ELISA to determine their ability to bind to 1E4. The results indicate that all identified 1E4-specific phage clones were able to bind to 1E4. To determine whether identified 1E4-specific phage clones can specifically mimic the protective epitopes of PI Ag, the selected phage clones were further tested for their binding ability with 1E4 to compete against binding with PI Ag by a competitive inhibition ELISA. Approximately $10^{10}$ of purified phage particles in 0.05 M carbonate/bicarbonate coating buffer (pH 9.6) were coated in a 96-well microtiter plate at 4° C. overnight. One hundred microliters of 5 m/ml 1E4 with or without 2 μg/ml of PI antigen was added into the wells of the phages coated plate. The binding abilities of 1E4 with or without PI antigen were detected with horseradish peroxidase-conjugated anti-mouse IgG. The inhibition index (A490 without PI-A490 with PI/A490 without PI) was used to evaluate the ability of PI antigen to inhibit 1E4 binding with selected phage particles. FIG. 8(B) shows the ability of PI Ag to inhibit 1E4 binding with selected phage clones as measured by inhibition index (A490 without PI-A490, with PI/A490, without PI). The phage clones, m1E44 and m1E41920, showed the highest inhibition index, suggesting these two phage clones may contain mimic epitopes that bind to the same 1E4 binding site as PI-LPS.

Figure 9A:
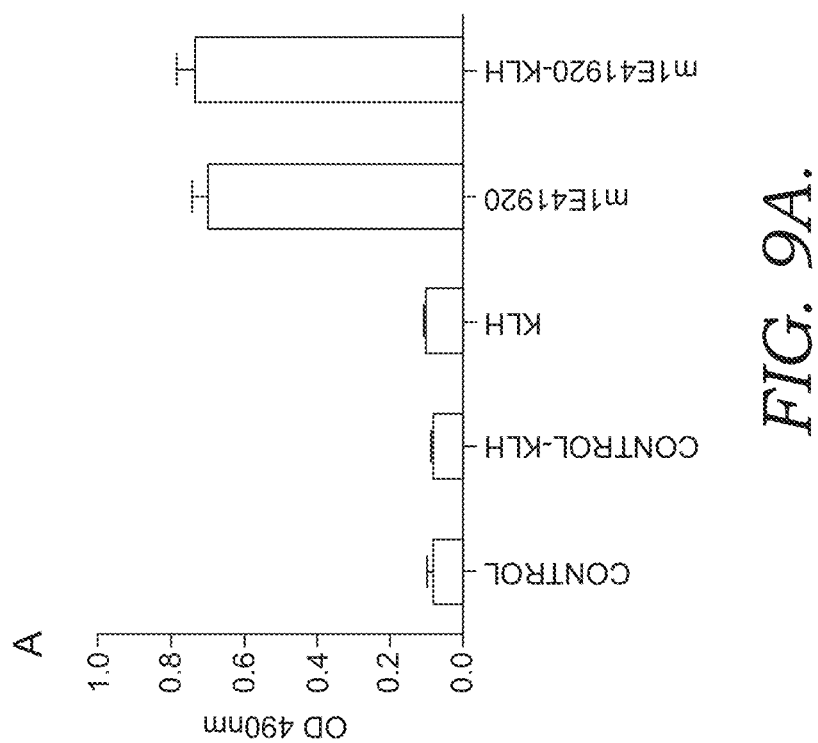
FIG. 9(A) evaluates the binding abilities of the synthetic mimic peptide m1E41920 and m1E41920-KLH conjugate with 1E4 by ELISA and competitive ELISA.
Figure 9B:
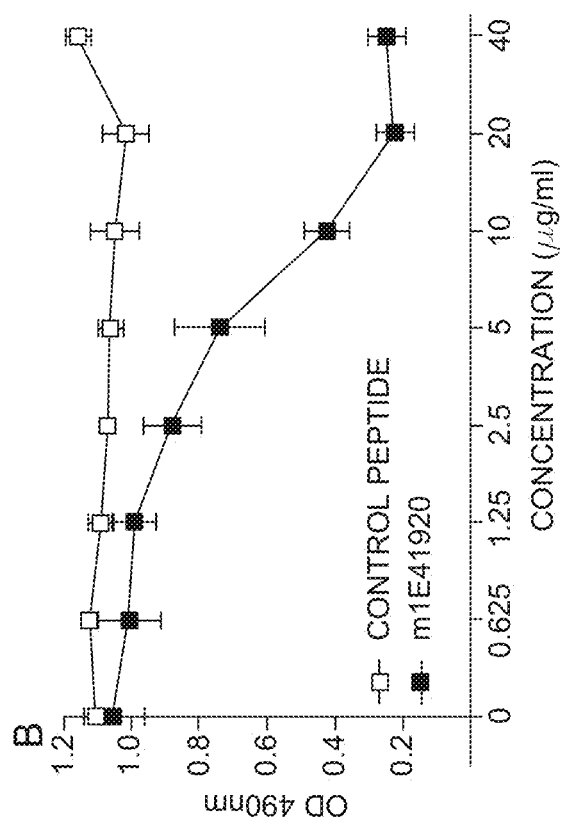
FIG. 9(B) evaluates the binding abilities of the synthetic mimic peptide m1E41920 and m1E41920-KLH conjugate with 1E4 by ELISA and competitive ELISA.

The mimotope, m1E41920 has been chemically synthesized and conjugated to Keyhole limpet hemocyanin (KLH) for further examining its immunogenicity. Refer to FIGS. 9(A) and 9(B), which evaluate the binding abilities of the synthetic mimic peptide m1E41920 and m1E41920-KLH conjugate with 1E4 by ELISA and competitive ELISA. The m1E41920, m1E41920-KLH, control peptide, control peptide-KLH, or KLH was coated in a 96-well microtiter plate at 4° C. overnight. The mAb 1E4 was added into the synthetic peptide-coated plate. The binding ability of 1E4 with synthetic peptides was detected with HRP-conjugated anti-mouse IgG. In addition, the synthetic m1E41920 was further tested for its binding ability with 1E4 to compete against binding with PI Ag by a competitive inhibition ELISA. The mAb 1E4 was mixed with different concentrations of m1E41920 or control peptide and added into a 96-well microtiter plate that was coated with PI Ag. The ability of m1E41920 to inhibit 1E4 binding with PI Ag was detected with HRP-conjugated anti-mouse IgG. ELISA analysis (FIG. 9(A)) indicated that both synthetic peptide m1E41920 and m1E41920-KLH conjugate specifically bound to 1E4, suggesting that m1E41920 and m1E41920-KLH conjugate retain their binding ability to 1E4. Competitive inhibition ELISA analysis (FIG. 9(B)) demonstrated that m1E41920 was able to inhibit the binding of 1E4 to PI antigen in a dose dependent manner. These results suggest that synthetic m1E41920 peptide can mimic the C. burnetii specific epitope on PI antigen.

Figure 10A:
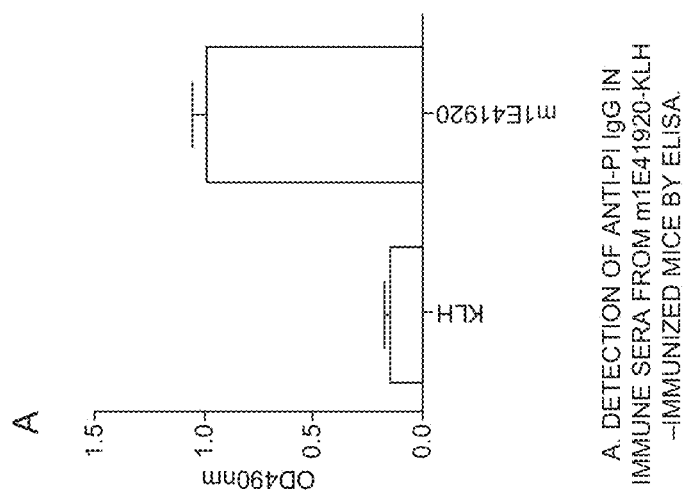
FIG. 10(A) is the analyses of m1E41920-KLH elicited antibody response to PI antigen.
Figure 10B:
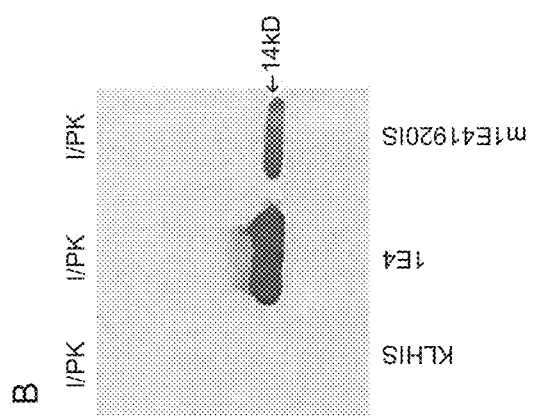
FIG. 10(B) is the analyses of m1E41920-KLH elicited antibody response to PI antigen.
Figure 10C:
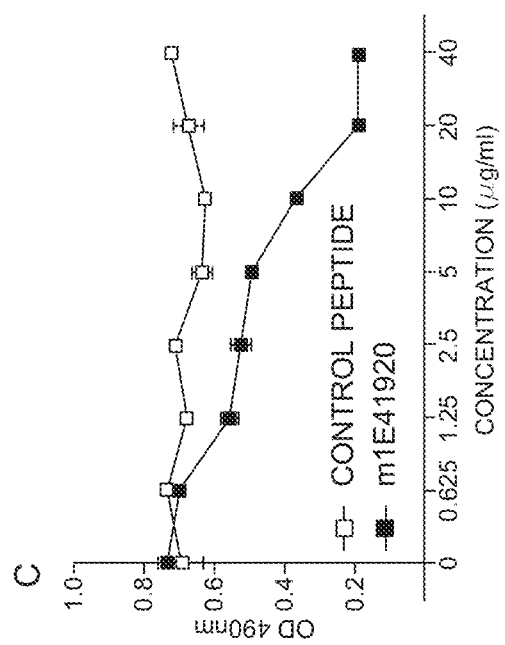
FIG. 10(C) is the analyses of m1E41920-KLH elicited antibody response to PI antigen.

Another embodiment further provides the analyses of m1E41920-KLH elicited antibody response to PI antigen. Turning now to FIGS. 10(A) to 10(C), ELISA analysis indicates that m1E41920-KLH was able to elicit specific IgG response against PI antigen. Western blotting showed that immune sera from m1E41920-KLH-immunized mice reacted with a 14 kDa proteinase K resistant band, which is identical to 1E4 recognized antigen. Competitive inhibition ELISA result demonstrated that m1E41920 was able to inhibit the binding of immune sera from m1E41920-KLH-immunized mice to PI antigen in a dose dependent manner, while the peptide control did not inhibit immune sera from m1E41920-KLH-immunized mice bind to PI antigen. These results further prove that synthetic m1E41920 peptide mimics epitopes on PI-LPS.

Figure 11A:
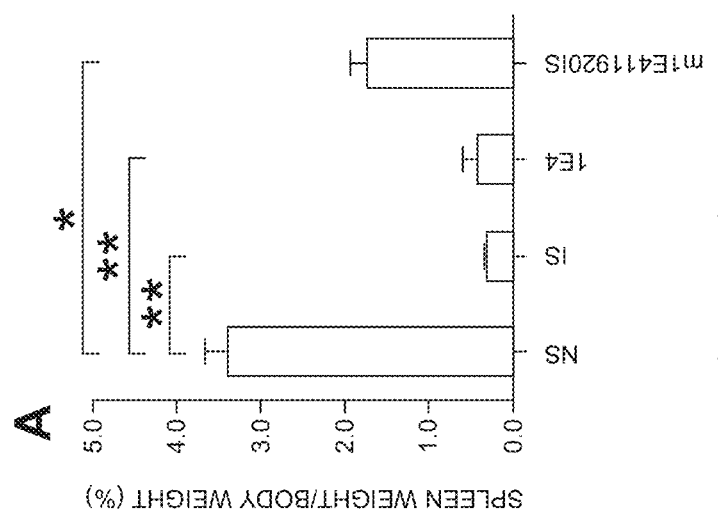
FIG. 11(A) evaluates the ability of immune sera from m1E41920-KLH-immunized mice to inhibit *C. burnetii* infection in BALB/c mice, both splenomegaly and with real-time-PCR.
Figure 11B:
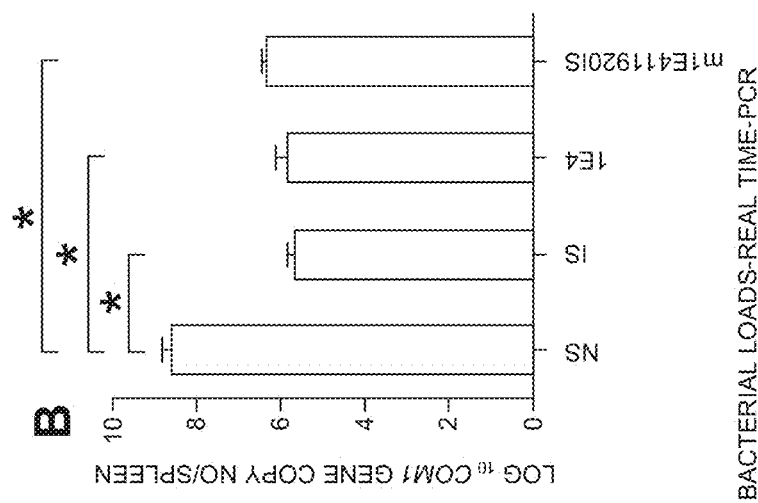
FIG. 11(B) evaluates the ability of immune sera from m1E41920-KLH-immunized mice to inhibit *C. burnetii* infection in BALB/c mice, both splenomegaly and with real-time-PCR.
Figure 11C:
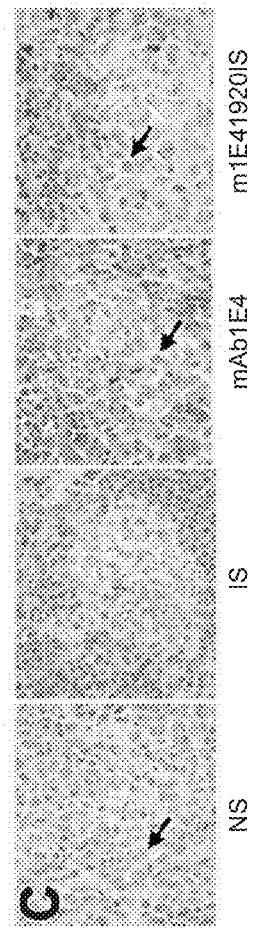
FIG. 11(C) evaluates the ability of immune sera from m1E41920-KLH-immunized mice to inhibit *C. burnetii* infection in BALB/c mice, both splenomegaly and with real-time-PCR.

In another embodiment, it has also been determined that m1E41920-KLH can induce a specific Ab response against PI antigen. Turning to FIGS. 11(A) and 11(B), evaluating the ability of immune sera from m1E41920-KLH-immunized mice to inhibit C. burnetii infection in BALB/c mice, both splenomegaly and with real-time-PCR, is shown. Compared to mice infected with normal mouse sera-treated C. burnetii, splenomegaly and bacterial burden in the spleen were significantly reduced in mice infected with immune sera from PIV-vaccinated mice, 1E4 or immune sera from m1E41920-KLH-immunized mice-treated C. burnetii. These results demonstrate that immune sera from m1E41920-KLH-immunized mice were able to inhibit C. burnetii infection, suggesting that m1E41920 specifically mimics the protective epitope on PI-LPS. For FIGS. 11(A) and 11(B), *p<0.05 and **p<0.01. As shown in FIG. 11(C), histopathological differences were observed in the spleen between mice infected with normal mouse sera-treated C. burnetii and mice infected with immune sera-treated C. burnetii. There were more and larger multifocal accumulations of macrophages (arrow) in red pulp of spleens of mice infected with normal mouse sera-treated C. burnetii than mice infected with immune sera from PIV-vaccinated mice, 1E4, or immune sera from m1E41920-KLH-immunized mice-treated C. burnetii. This indicates that immune sera from PIV-vaccinated mice, 1E4, or immune sera from m1E41920-KLH-immunized mice provided similar levels of protection against C. burnetii challenge-induced inflammatory responses. These results indicate that immune sera from m1E41920-KLH-immunized mice was able to inhibit C. burnetii infection in vivo, whereas immune sera from PIV-vaccinated mice or 300 µg 1E4 had a stronger ability than immune sera from m1E41920-KLH-immunized mice to inhibit C. burnetii infection. These results suggest that m1E41920 specifically may mimic the protective epitope of PI-LPS. For FIG. 10(C), pathological changes in the spleen were at 14 days post-challenge. The data presented in each group are the average with SD of four mice. Original magnification ×400.

Figure 12A:
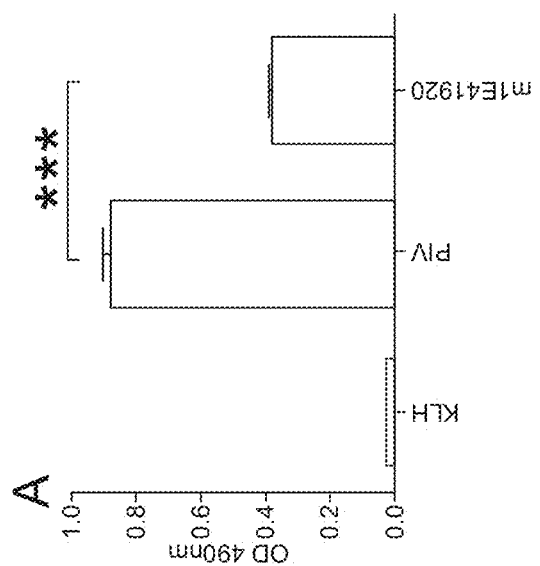
FIG. 12(A) evaluates the protective efficacy of m1E41920-KLH against *C. burnetii* infection in BALB/c mice.
Figure 12B:
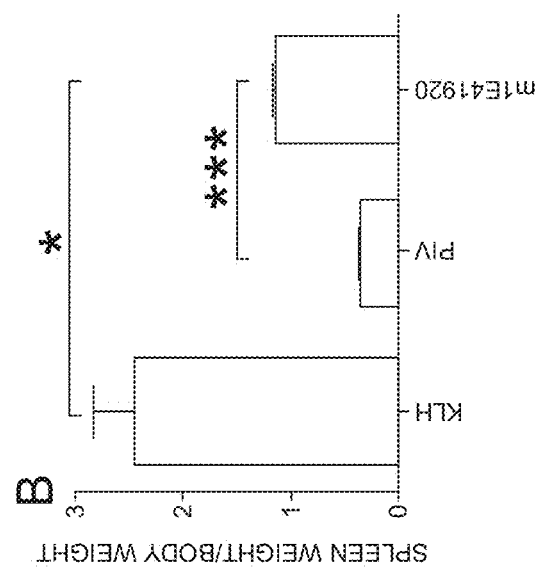
FIG. 12(B) evaluates the protective efficacy of m1E41920-KLH against *C. burnetii* infection in BALB/c mice.
Figure 12C:
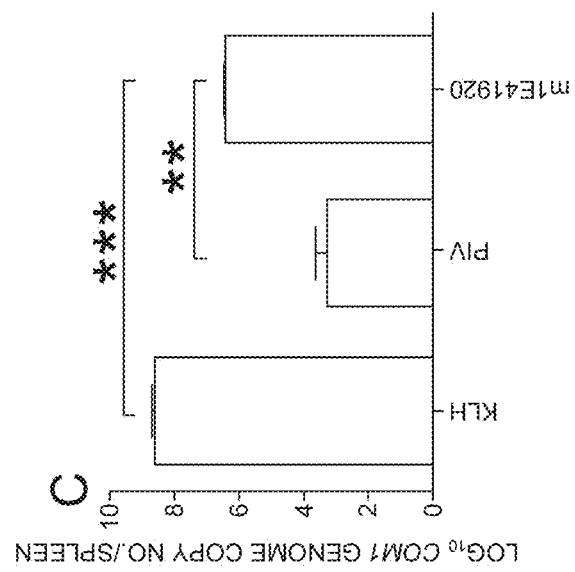
FIG. 12(C) evaluates the protective efficacy of m1E41920-KLH against *C. burnetii* infection in BALB/c mice.
Figure 12D:
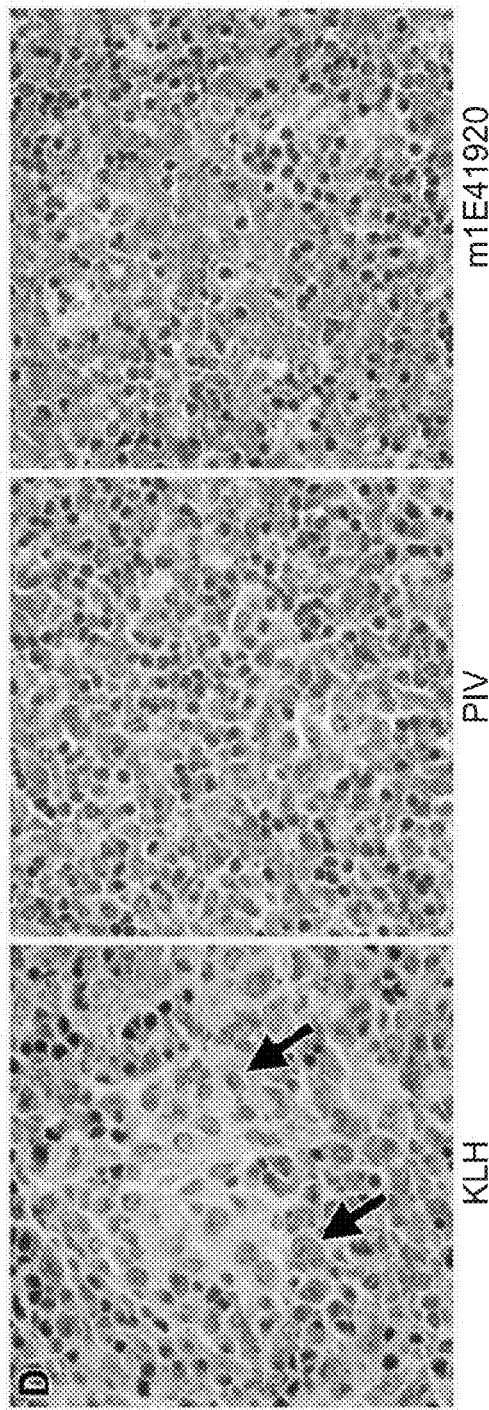
FIG. 12(D) evaluates the protective efficacy of m1E41920-KLH against *C. burnetii* infection in BALB/c mice.

One embodiment further teaches m1E41920-KLH is able to confer protection against C. burnetii infection, thus a protective antigen against Q fever. Turning to FIGS. 12(A) to 12(C), evaluation of the protective efficacy of m1E41920-KLH against C. burnetii infection in BALB/c mice is shown. Compared to KLH-immunized control mice (FIG. 12(A)), splenomegaly and the bacterial burden in the spleen were significantly reduced in m1E41920-KLH-vaccinated mice (FIGS. 12(B) and 12(C)). This result suggests that m1E41920-KLH is a protective antigen and a candidate for developing a safe and effective peptide mimic vaccine to prevent human Q fever. For FIGS. 12(A) to 12(C), *p<0.05, p<0.01 and *p<0.001. In addition, multifocal accumulations of large macrophages (arrow) were present in red pulp of spleens of KLH-immunized mice, but not in PIV- or m1E41920-KLH-immunized mice (FIG. 12(D)), which indicates that PIV- or m1E41920-KLH-immunized mice provided similar levels of protection against C. burnetii challenge-induced inflammatory responses. These results suggest that m1E41920-KLH was able to confer significant protection against C. burnetii challenge, but the levels of protection were lower than PIV. For FIG. 12(D), pathological changes in the spleen were at 14 days post-challenge. The data presented in each group are the average with SD of four mice. Original magnification ×400.

Another embodiment further provides a general method for identifying and generating new vaccines to prevent diseases caused by LPS-based intracellular Gram-negative bacteria besides C. burnetii. The method comprises the steps of identifying a protective monoclonal antibody specific to a LPS of a specific intracellular Gram-negative bacteria that causes the specific LPS-based intracellular Gram-negative bacterial infection in the subject; identifying one or more mimetic peptides by screening a Phage Display Library with the protective monoclonal antibody; and evaluating the one or more mimetic peptides to identify the one or more mimetic peptides that confer an effective protective antigen against the specific LPS-based intracellular Gram-negative bacterial infection in the subject. An effective protective antigen against the specific LPS-based intracellular Gram-negative bacterial infection in the subject is a protective antigen that prevents infection in a subject by the Gram-negative bacterium.

In one embodiment, the Phage Display Library is a Ph.D.-12 Phage Display Peptide Library. One or more mimetic peptides from the screening of the Phage Display Peptide Library comprise the following peptide sequences: SWFHPQRRHSHQ (SEQ ID NO: 9), SWMPHPRWSPQH (SEQ ID NO: 10), MHRAPSTHKLLP (SEQ ID NO: 11), ASWHQHYMKHKP (SEQ ID NO: 12), SEFHRHGDKEHK (SEQ ID NO: 13), CEFPRSWDMETN (SEQ ID NO: 14), SLTRHKPEPHRK (SEQ ID NO: 15), SLTWHKHELHRK (SEQ ID NO: 7), SPPWHKHELHRK (SEQ ID NO: 8), GGWHKHISRSDP (SEQ ID NO: 16), YHKHPHTYHNFK (SEQ ID NO: 17), HPKHPHTHTNDQ (SEQ ID NO: 18), HMHMHQHVAQTQ (SEQ ID NO: 19), HMGMTKINYSAL (SEQ ID NO: 20), SNYSDVKRLPTV (SEQ ID NO: 21), and SVNWQKQTISNL (SEQ ID NO: 22). In yet another embodiment, the protective monoclonal antibody is 1E4 and is comprised of polypeptide sequences of SEQ ID NO: 1 and SEQ ID NO: 2, or polypeptide sequences having at least 90% identity to the polypeptide sequences of SEQ ID NO: 1 and SEQ ID NO: 2. In another embodiment, the protective monoclonal antibody 1E4 comprises nucleotide sequences of SEQ ID NO: 3 and SEQ ID NO: 4, or nucleotide sequences having at least 90% identity to the nucleotide sequences of SEQ ID NO: 3 and SEQ ID NO: 4, which encode the polypeptide sequences of SEQ ID NO: 1 and SEQ ID NO: 2, respectively.

In another embodiment, there is a composition for protection against C. burnetti infection in a subject comprising a peptide with a sequence of SLTWHKHELHRK (SEQ ID NO: 7) or SPPWHKHELHRK (SEQ ID NO: 8), or a peptide sequence having at least 90% identity to SLTWHKHELHRK (SEQ ID NO: 7) or SPPWHKHELHRK (SEQ ID NO: 8). In one embodiment, the composition comprises the peptide with the sequence SLTWHKHELHRK (SEQ ID NO: 7) that is conjugated to Keyhole limpet hemocyanin (KLH). In another embodiment, the subject is one or more of mice, guinea pigs or humans. In a further embodiment, the peptide comprising the peptide sequence of SLTWHKHELHRK (SEQ ID NO: 7) binds to 1E4 antibody. In one embodiment, the peptide comprising the peptide sequence of SLTWHKHELHRK (SEQ ID NO: 7) conjugated to KLH binds to 1E4 antibody. In another embodiment, the peptide contains a W/HXH motif, where X represents any amino acid.

Although the peptide mimics have been considered as potential surrogate antigens of carbohydrates for vaccine development against several microorganisms, only few studies have achieved protective efficacy testing of mimetic peptides. Previous studies suggested that the most widely used parameters for selecting peptide mimics, such as high-affinity binding to a relevant anti-carbohydrate antibody, competition with native carbohydrate antigen for antibody binding, and induction of robust anti-peptide response, maybe insufficient and not predictive of whether a mimetic peptide is capable of eliciting an protective carbohydrate cross-reactive immune response.

The mimotope vaccine strategies are based on the concept of reverse vaccinology, in which protective Abs can be used as probes to identify mimetic peptides that can re-induce protective Ab responses in vivo. The aforementioned results against *C. burnetii* demonstrate that the identification of protective mAb 1E4 led to the identification of protective mimic peptide m1E41920, suggesting that using protective Abs as probes is critical to identify protective mimetic peptides.

In addition, the sequencing analysis and computational docking results provide theoretical evidence to support that m1E41920 cannot only simulate the sugar cyclic structures through the imidazole ring of histidine in W/HXH motif, but also can simulate the mAb/LPS recognition through binding of the same HCDR3 residues. These characteristics may contribute more to the successful identification of the protective mimic peptide in this location. The mimetic peptide m1E41920 fits well into the binding site of the parent mAb 1E4 $V_H$ chain. The directly contacted m1E41920 and 1E4 $V_H$ residues were identified and there was no direct contacted residue in the 1E4 $V_L$ chain. The model docking structure of the 1E4-m1E41920 complex shows that the mimetic peptide m1E41920 fits into the H chain groove with the middle four-residue domain (WHKH) in a helix turn, whereas it directly contacts HCDR1, HCDR2, and HCDR3 in an extended conformation through the N-terminal domain SLTWH and C-terminal domain -L-R-, respectively. This suggests that the m1E41920 central domain is necessary to maintain the conformation, and the two terminal domains are involved in binding to HCDRs.

The automatic modeling of 1E4 variable domains was established by canonical structure method from RosettaAntibody. The structure of mimetic peptide m1E41920 was modeled using SAM-T08. The two predicted Brookhaven Protein Data Bank files were loaded onto the RosettaDock web server to obtain the 1E4-m1E41920 complex model. Structure analysis and graphical renderings of the top one docking prediction were performed by using PyMOL.

In one embodiment, the protective epitopes on PI-LPS were identified to prove the concept that peptide mimics of PI-LPS can confer protective immunity against *C. burnetii* infection; a novel protective mAb that recognizes a PI-specific epitope on PI-LPS was developed and identified a protective peptide mimic of PI-LPS by screening a phage display library with the protective mAb. To our knowledge, this study provides the first evidence to demonstrate that there is a protective epitope on PI-LPS and prove the feasibility of development of a peptide mimic vaccine against Q fever.

Several PI-LPS-specific mAbs have been developed for analysis of antigenicity of immunogenic components of *C. burnetii* LPS and detection of the virulent form of *C. burnetii*. Hotta et al. reported generation of 19 PI-LPS-specific mAbs and demonstrated that these mAbs were able to be separated into three groups based on their reactivity with O-polysaccharide chains (27 kDa of PI-LPS), O-polysaccharide chains (15-27 kDa of PI-LPS), and outer-core oligosaccharides (14 kDa of PI-LPS). Palkovicova et al. developed a virenose-targeted mAb (IgG2b subclass) that recognized O-polysaccharide chains and suggested that this virenose-unique mAb may be a useful biomarker for detection of virulent *C. burnetii*. However, it still remains unknown whether PI-LPS-recognized mAbs are protective. The aforementioned methods may be employed to identify and generate peptide-based vaccines against *Salmonella enteritidis*, *Mycobacterium tuberculosis*, *Francisella tularensis*, *Chlamydia trachomatis* and *Brucella abortus*.

m1E41920 Fits Well into the 1E4 Groove in the Docking Model

Figure 13A:
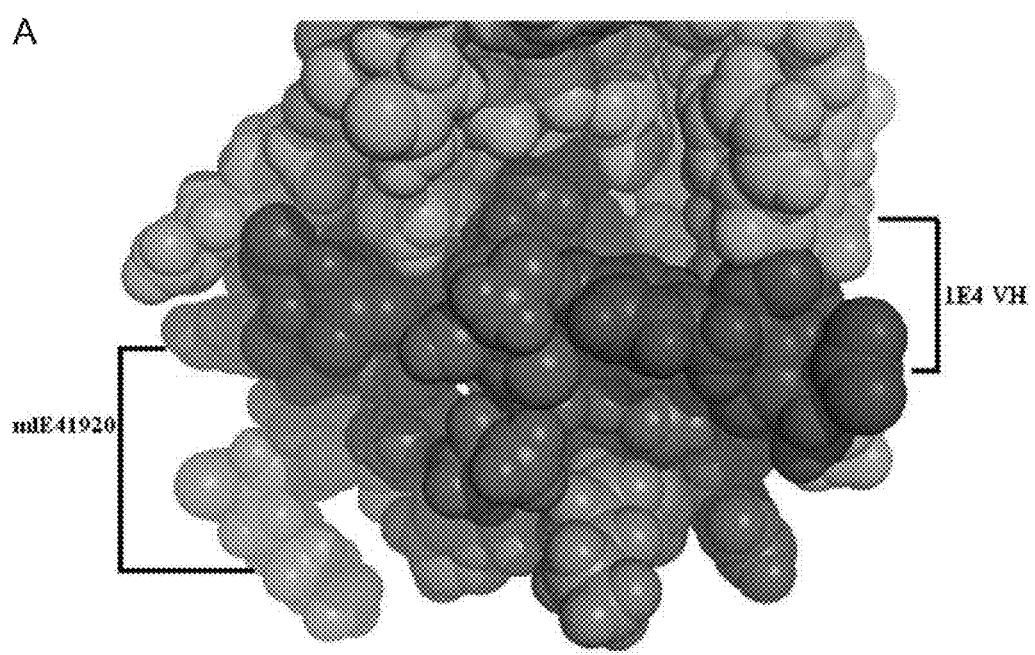
FIG. 13(A) are is a model of 1E4-m1E41920 complex established by the molecular modeling and docking procedures.
Figure 13B:
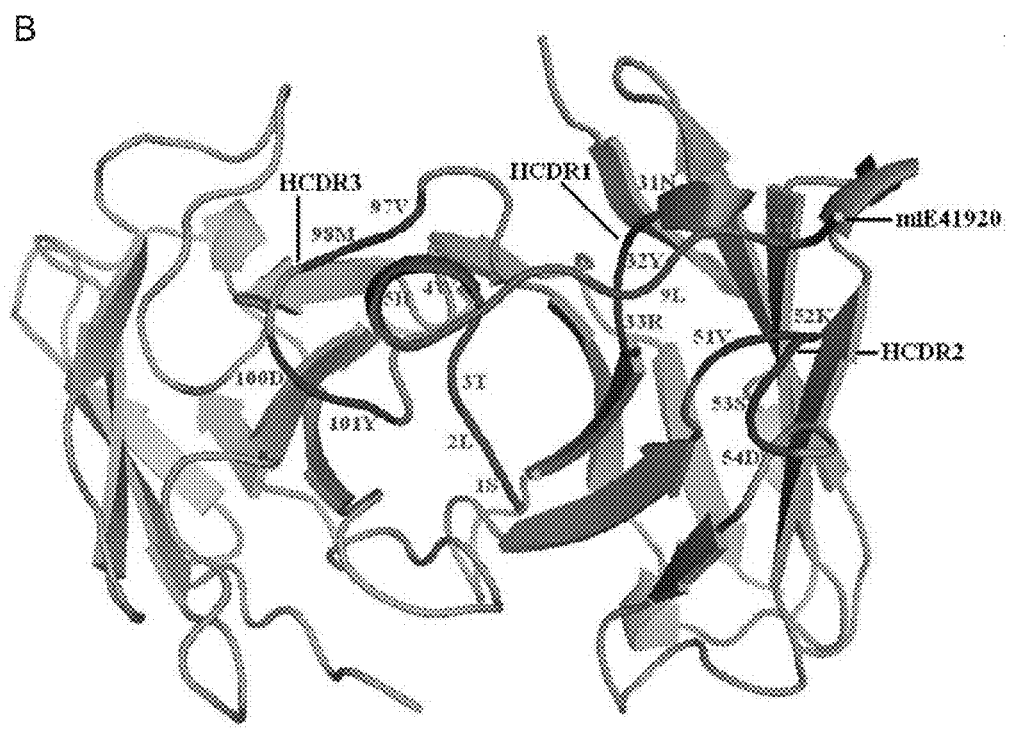
FIG. 13(B) is a model of 1E4-m1E41920 complex established by the molecular modeling and docking procedures.

As shown in FIG. 13, the mimetic peptide m1E41920 fits well into the binding site of the parent mAb 1E4 $V_H$ chain. The directly contacted m1E41920 and 1E4 VH residues were identified and displayed as red and blue spacefill graphs, respectively (FIG. 13(A)), although there was no direct contacted residue in the 1E4 $V_L$ chain (data not shown). The model docking structure of the 1E4-mE41920 complex was displayed as a cartoon graph in FIG. 13(B). The mimetic peptide m1E41920 fits into the H chain groove with the middle four-residue domain (WHKH) in a helix turn, whereas it directly contacts HCDR1, HCDR2, and HCDR3 in an extended conformation through the N-terminal domain SLTWH and C-terminal domain -L-R-, respectively. This suggests that the m1E41920 central domain is necessary to maintain the conformation, and the two terminal domains are involved in binding to HCDRs. It may also help to explain why m1E41920 is a stronger inhibitor, as only m1E41920 contains the complete motif SLTWH, which may be very important for the 1E4 binding. In addition, although 1E4 HCDR3 has 15 residues (FIG. 13(B)), only the four HCDR3 central residues (VM-DY), which are de novo generated by D-J conjugation and N insertion, directly contact five N-terminal residues (SLTWH) of m1E41920 (FIG. 13(B)). This suggests that m1E41920 can bind to the LPS binding site of 1E4. These data provide theoretical evidences to support the m1E41920 structural mimicry of PI-LPS based on its ability to bind to the same HCDR3 residues of 1E4. For FIG. 13(A), the images were generated using Pymol, and the 1E4-m1E41920 interaction model was shown as a spacefill graph. The directly contacted m1E41920 and 1E4 $V_H$ residues in direct contact were identified and displayed as red and blue spacefill graph, respectively. The contacted residues of the 1E4 $V_H$ paratopes in complex with m1E41920 are shown in blue, and the remainders are shown in green. The peptide mimic m1E41920 fits well into the binding site of the parent mAb 1E4 $V_H$ chain. For FIG. 13(B), the model docking structure of the 1E4-m1E41920 complex was displayed as a cartoon graph. The contacted residues and amino acid abbreviations are shown in the corresponding color described in (A). The peptide mimic m1E41920 fits into the H chain groove with the middle four residue domain (WHKH) in a helix turn, whereas it directly contacts HCDR1, HCDR2, and HCDR3 in an extended conformation through the N-terminal domain SLTWH and C-terminal domain -L-R-, respectively.

Characterization of Fab1E4, muscFv1E4 and huscFv1E4

Expression and purification of recombinant muscFv1E4 and huscFv1E4: *Escherichia coli* strain BL21 was transformed with pETmuscFv1E4 or pEThuscFv1E4 and then incubated at 37° C. in 2×YT broth with ampicillin. When the optical density reached 0.6 at a wavelength of 600 nm, IPTG (isopropyl-1-thio-β-D-galactopyranoside) was added to the culture at a final concentration of 1 mM and the cells were further grown overnight at 25° C. Pelleted cells were suspended in 10 ml of ice-cold periplasmic extraction buffer [30 mM Tris-HCl (pH 8.0), 20% (w/v) sucrose, 1 mM EDTA], 200 units of lysozyme (Epicentre, Madison, Wis.) were added and incubated at room temperature (RT) for 10 min. Lysozyme-treated bacteria were pelleted by centrifugation and the supernatant was dialyzed overnight against PBS at 4° C. Recombinant muscFv1E4 and huscFv1E4 were purified under native conditions using Ni-NTA HisBind Resins (Novagen) according to the manufacturer's instructions.

Purified 1E4, Fab1E4, muscFv1E4 and huscFv1E4 were resuspended in reduced loading buffer and separated by 12% SDS-PAGE gels using a Mini-PROTEANII apparatus (BIO-RAD LABORATORIES). The purity of purified 1E4, Fab1E4, muscFv1E4 and huscFv1E4 was analyzed by Coomassie blue-staining of SDS-PAGE gel. For Western blotting, samples were separated by SDS-PAGE and transferred electrophoretically onto nitrocellulose membranes in Tris-glycine buffer. The membranes were blocked for 1 h at room temperature (RT) in PBS with 0.05% Tween 20 (PBST) and 10% nonfat dry milk and then incubated with 1:2000 diluted mouse anti-6×His epitope tag mAb (THERMO FISHER SCIENTIFIC) at 4° C. overnight. After washing five times (5 min each wash) with PBST buffer, the membranes were incubated with horseradish peroxidase (HRP)-conjugated goat anti-mouse IgG (1:10,000 dilution) (SOUTHERN BIOTECH, Birmingham, Ala.) for 1 h at RT. The reactions were detected by using an ECL Western blot detection kit (THERMO FISHER SCIENTIFIC).

Figure 14A:
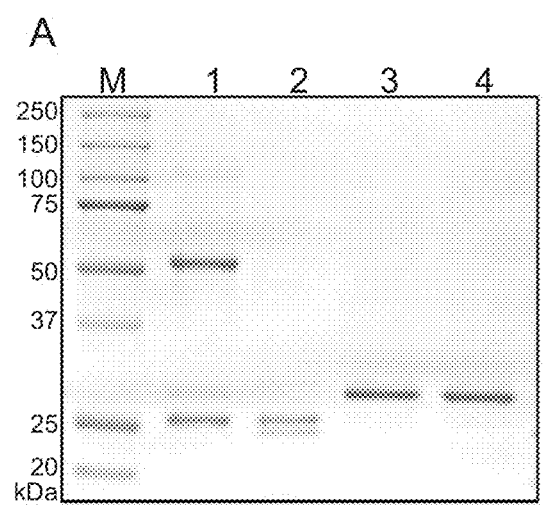
FIG. 14(A) characterizes Fab1E4, muscFv1E4 and huscFv1E4.
Figure 14B:
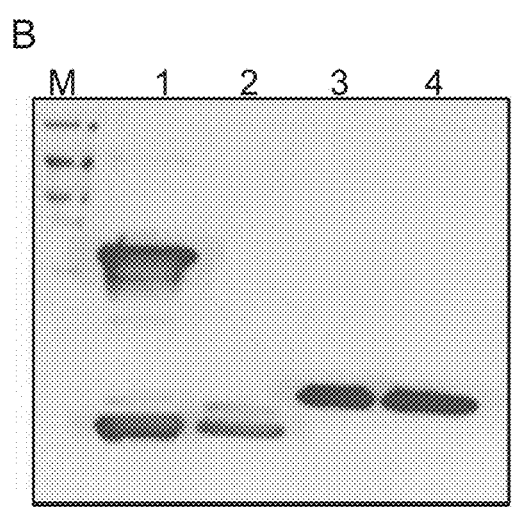
FIG. 14(B) characterizes Fab1E4, muscFv1E4 and huscFv1E4.

In order to examine the ability of Fab1E4, muscFv1E4 and huscFv1E4 to inhibit C. burnetii infection, the purity and specificity of purified Fab1E4, muscFv1E4 and huscFv1E4 were analyzed by SDS-PAGE and Western blotting. A shown in FIG. 14(A), two bands of 50 kDa heavy chains and 25 kDa light chains were observed in 1E4 preparation (lane 1). Two similar ~25 kDa bands showing dissociated light (VL-Cκ) and heavy changes (VH-CH1) were detected in purified Fab1E4 fragments (lane 2). As expected, a 30 kDa band was observed in the purified recombinant muscFv1E4 (lane 3) and huscFv1E4 (lane 4). FIG. 14(B) shows that both 50 kDa heavy chains and 25 kDa light chains of 1E4 (lane 1) and both the VL-Cκ and VH-CH1 of Fab1E4 (lane 2) reacted with goat anti-mouse IgG in Western blotting as predicted. Western blotting analysis also indicated that purified muscFv1E4 and huscFv1E4 reacted with anti-6×His mAb (FIG. 14(B), lanes 3 & 4). In addition, the nucleotide sequencing results and deduced amino acid sequences demonstrated that the assembled muscFv1E4 gene was correctly constructed and that the variable regions of heavy and light changes were productively rearranged with the linker sequence (data not shown). These results confirmed the purity and specificity of purified Fab1E4, muscFv1E4 and huscFv1E4.

Figure 14C:
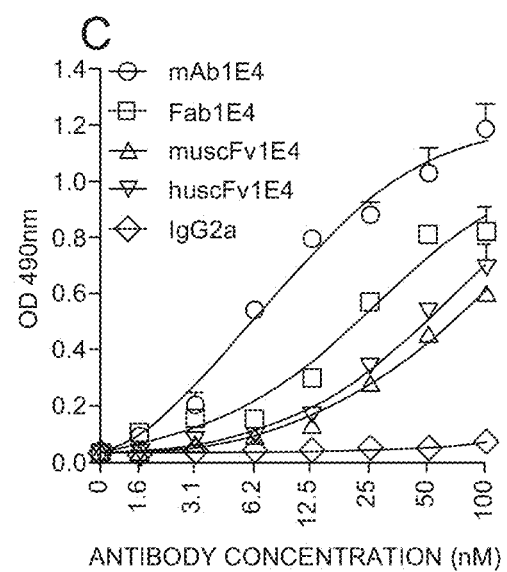
FIG. 14(C) characterizes Fab1E4, muscFv1E4 and huscFv1E4.
Figure 14D:
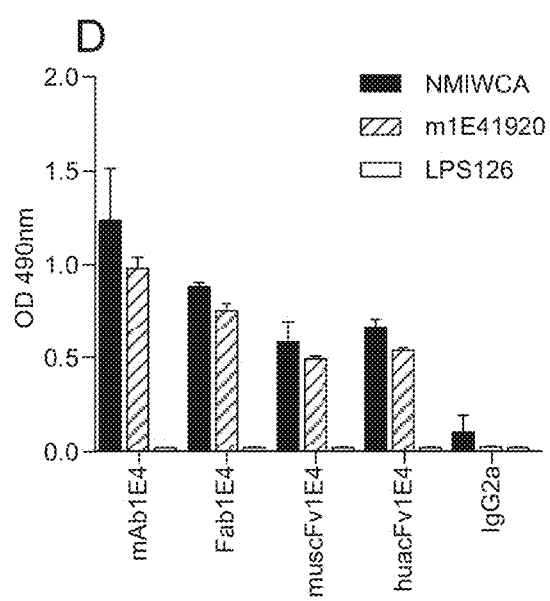
FIG. 14(D) characterizes Fab1E4, muscFv1E4 and huscFv1E4.

Next, the m1E41920 peptide was used to evaluate the binding ability of Fab1E4, muscFv1E4 and huscFv1E4 by indirect ELISA. As shown in FIG. 14(C), 1E4, Fab1E4, muschFv1E4 and huscFv1E4 were able to bind to m1E41920 in a dose dependent manner but the binding capacity differed among 1E4, Fab1E4, muscFv1E4 and huscFv1E4. The nonlinear regression derived by GraphPad Prism analysis showed 1E4 had the lowest half maximal effective concentration (EC50, the concentration needed to achieve 50% maximal binding) of 6.82 nM to m1E41920, while the EC50s were 26.85 nM, 73.10 nM and 62.29 nM for Fab1E4, muscFv1E4 and huscFv1E4, respectively. These results suggest that the binding capability to m1E41920 is similar between muschFv1E4 and huscFv1E4 but is lower than Fab1E4. In addition, we also examined whether Fab1E4, muscFv1E4 and huscFv1E4 can specifically bind to C. burnetii native antigen (PI whole cell antigen) by indirect ELISA. As shown in FIG. 14(D), Fab1E4, muscFv1E4 and huscFv1E4 were able to specifically bind to both PI whole cell antigen and m1E41920, however, their binding capability was lower than 1E4. These results suggest that Fab1E4, muscFv1E4 and huscFv1E4 retain a comparable binding activity to mimetic peptide and native antigen as 1E4.

Indirect ELISA was performed as follows: Briefly, 5 μg/ml PI whole cell antigen or 50 μg/ml synthetic mimetic peptide in 100 μl 0.05 M carbonate/bicarbonate coating buffer (pH 9.6) was added to each well of a 96-well microtiter plate and coated at 4° C. for 48 h. Plates were then blocked with 1% BSA in PBST buffer (0.05% Tween 20 in PBS) for 1 hour at 37° C. and incubated with 100 ul of differing concentrations of 1E4, Fab1E4, muscFv1E4 or huscFv1E4 at 4° C. overnight. After washing four times (5 min each wash) with PBST buffer, 100 μl of anti-6×His mAb (1:2000) was added to each well and incubated at 37° C. for 2 h. Following washing five times with PBST buffer, the plates were incubated with 100 ul of HRP-conjugated goat anti-mouse IgG (1:2000) at 37° C. for another 2 h. After washing five times with PBST buffer, the Sigma Fast 0-Phenylenediamine Dihydrochloride Tablet Sets (SIGMA-ALDRICH) were used as substrates and the OD was measured at 490 nm by the SPECTRA MAX M2 system (MOLECULAR DEVICES CORPORATION, Sunnyvale, Calif.).

Figure 15A:
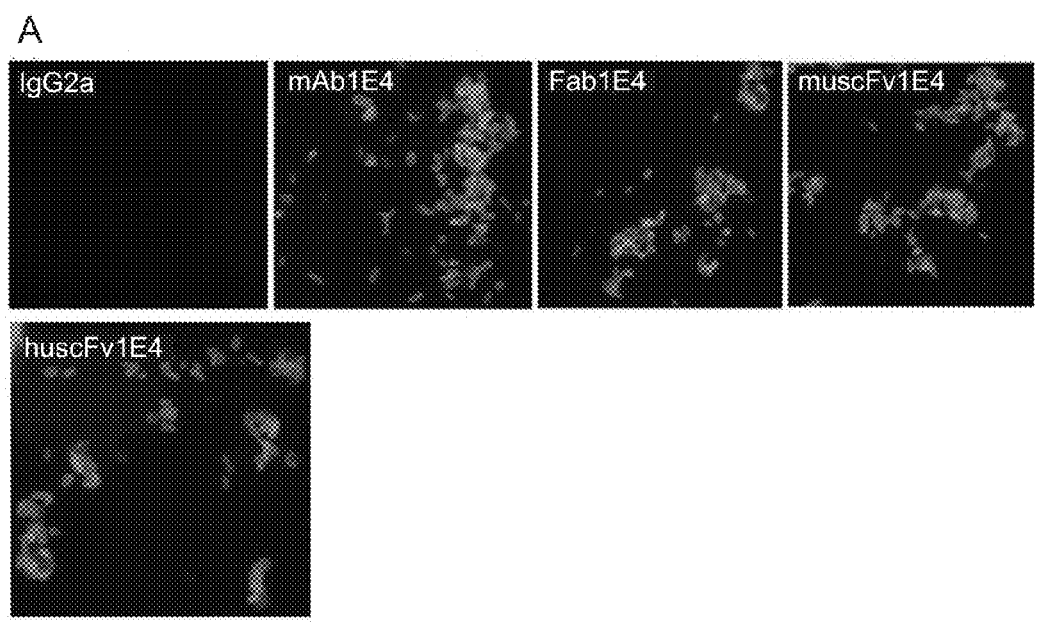
FIG. 15(A) evaluates the ability of 1E4, Fab1E4, muscFv1E4 and huscFv1E4 to inhibit *C. burnetii* infection in vivo.
Figure 15B:
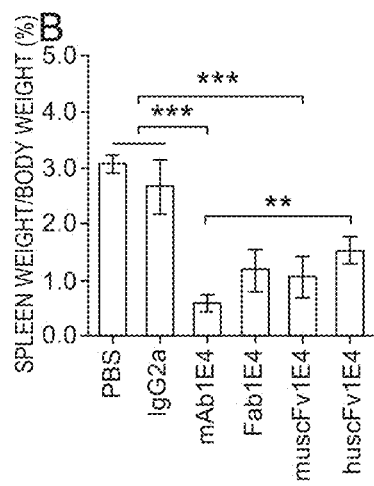
FIG. 15(B) evaluates the ability of 1E4, Fab1E4, muscFv1E4 and huscFv1E4 to inhibit *C. burnetii* infection in vivo.
Figure 15C:
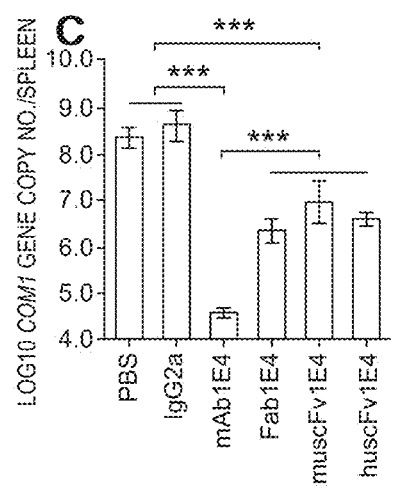
FIG. 15(C) evaluates the ability of 1E4, Fab1E4, muscFv1E4 and huscFv1E4 to inhibit *C. burnetii* infection in vivo.
Figure 15D:
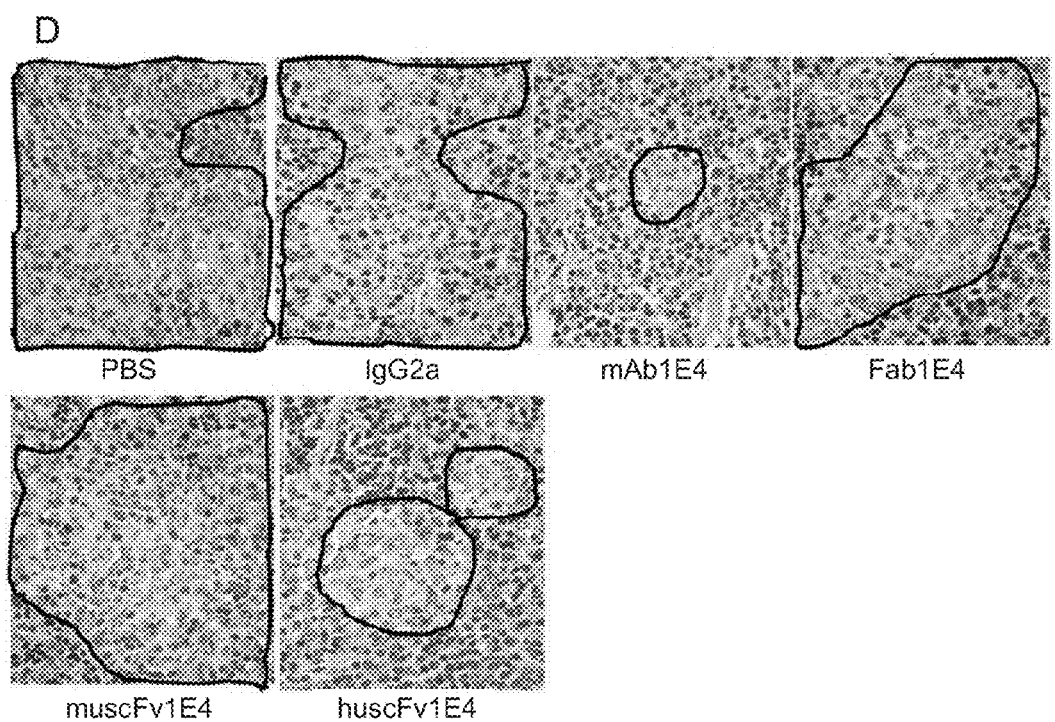
FIG. 15(D) evaluates the ability of 1E4, Fab1E4, muscFv1E4 and huscFv1E4 to inhibit *C. burnetii* infection in vivo.
Figure 15E:
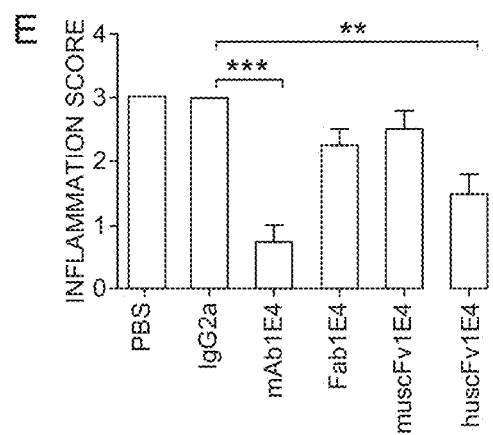
FIG. 15(E) evaluates the ability of 1E4, Fab1E4, muscFv1E4 and huscFv1E4 to inhibit *C. burnetii* infection in vivo.

To determine whether Fab1E4, muscFv1E4 and huscFv1E4 retain the ability of 1E4 to inhibit C. burnetii infection in vivo, we examined if treatment of virulent C. burnetii with Fab1E4, muscFv1E4 or huscFv1E4 would inhibit C. burnetii infection in mice. Before infection of mice with Ab treated C. burnetii, IFA was used to confirm whether 1E4, Fab1E4, muschFv1E4 and huscFv1E4 can specifically bind to live virulent C. burnetii. As shown in FIG. 15(A), the C. burnetii immune complex formation was detected in 1E4, Fab1E4, muscFv1E4 or huscFv1E4 treated C. burnetii but was not detected in IgG2a isotype control of PBS treated C. burnetii (data not shown). These results suggest that 1E4, Fab1E4, muscFv1E4 and huschFv1E4 were able to specifically bind to live C. burnetii. As shown in FIG. 15(B), compared to mice infected with PBS or IgG2a isotype control treated C. burnetii, splenomegaly was significantly reduced in mice infected with 1E4, Fab1E4, muscFv1E4 or huscFv1E4 treated C. burnetii (p<0.001). In addition, splenomegaly in mice infected with huscFv1E4 treated C. burnetii was similar to mice infected with Fab1E4 or muscFv1E4 treated C. burnetii but it was significantly greater than in mice infected with 1E4 treated C. burnetii. In support of the splenomegaly results, compared to mice infected with PBS or IgG2a isotype control treated C. burnetii, significantly lower C. burnetii genome copies were detected in spleens from mice infected with 1E4, Fab1E4, muscFv1E4 or huscFv1E4 treated C. burnetii. While the C. burnetii load in spleen was not significantly different among mice infected with Fab1E4, muscFv1E4 or huscFv1E4 treated C. burnetii, it was significantly higher than in mice infected with 1E4 treated C. burnetii (FIG. 15C). FIG. 13D shows histopathological differences in the spleens from different groups of mice. Large numbers of moderate to large accumulations of macrophages (FIG. 15(D), encircled by a black border) were present in the red pulp of spleens form mice infected with C. burnetii treated by PBS, IgG2a isotype control, Fab1E4, or muscFv1E4. In contrast, only few small to moderate accumulations of macrophages (FIG. 15(D), encircled by a black border) appeared in the red pulp of spleens from mice infected with C. burnetii treated by 1E4 (p<0.001) or huscFv1E4 (p<0.01). As shown in FIG. 15(E), compared to mice infected with PBS or IgG2a isotype control treated C. burnetii, the inflammation score in the spleen was significantly lower in mice infected with 1E4 or huscFv1E4 treated C. burnetii, however, it was similar in mice infected with Fab1E4, or muscFv1E4 treated C. bur-

*netii*. These results indicate that although Fab1E4, muscFv1E4 and huscFv1E4 were able to inhibit *C. burnetii* infection in vivo, their ability to inhibit *C. burnetii* infection was lower than 1E4, suggesting both the variable region and Fc fragment may be required for 1E4 mediated protection in vivo. For FIGS. 15(B), 15(C) and 15(E), p<0.01 and *p<0.001.

Immunofluorescence assay (IFA): Infected cells were fixed with 2% paraformaldehyde for 15 min and permeabilized with cold methanol for 10 min. Rabbit anti-PI polyclonal antibodies (1:500) were used to stain intracellular *C. burnetii*, followed by incubation with 10 μg/ml FITC-labeled goat anti-rabbit IgG (1:1,000) (SOUTHERN BIOTECHNOLOGY, Birmingham, Ala.). Host nuclei were stained by DAPI in mounting medium (1:500) (INVITROGEN) and slides were examined by using fluorescence microscopy. In addition, IFA was also used to detect the *C. burnetii* immune complex formation. Briefly, live virulent *C. burnetii* organisms ($1 \times 10^7$) were incubated in 500 μl PBS with 1% BSA containing different concentrations of IgG2a isotype control, 1E4, Fab 1E4, muscFv1E4 or huscFv1E4 at 4° C. overnight. The mixture was spun at 15,000 rpm/min in a microfuge for 30 min, the pellets were spread on a cover slide and then fixed with 2% paraformaldehyde for 15 min. For the IFA, the pellets from the mixture of *C. burnetii* with IgG2a, 1E4 or Fab1E4 were directly stained with FITC labeled goat anti-mouse IgG, while the pellets from the mixture of *C. burnetii* with muscFv1E4 or huscFv1E4 were incubated with mouse anti-6×His mAb first and then stained with FITC labeled goat anti-mouse IgG. The binding of IgG2a isotype control, 1E4, Fab1E4, muscFv1E4 or huscFv1E4 with live virulent *C. burnetii* was examined by using fluorescence microscopy.

Quantitative PCR assay: High Pure PCR Template Preparation Kit (ROCHE MOLECULAR BIOCHEMICALS, Indianapolis, Ind.) with modifications was used for extraction of DNA templates from *C. burnetii* infected mouse tissues and cells. Real time-PCR was performed using Applied Biosystems 7300/7500 Real Time PCR System. The recombinant plasmid DNA (com1 gene ligated into pET23a vector) was used as a standard DNA to quantify com1 gene copy numbers in spleen samples.

To determine whether Fab 1E4, muscFv1E4 and huscFv1E4 retain the ability of 1E4 to inhibit *C. burnetii* infection in vivo, we examined if treatment of virulent NMI with Fab 1E4, muscFv1E4 or huscFv1E4 would inhibit *C. burnetii* infection in BALB/c mice. In order to compare the inhibition ability of Fab1E4, muscFv1E4 and huscFv1E4 with 1E4 in vivo, it is important to make sure that the same numbers of *C. burnetii* treated with different Ab will be injected into mice. Since aerosol infection cannot guarantee that mice will receive the same numbers of Ab treated *C. burnetii* between different experimental groups, this experiment was performed by i.p. injection. Since one molecule of 150 kDa 1E4 carries two antigen binding sites, and one molecule of either 50 kDa Fab1E4, 25 kDa muscFv1E4 or 25 kDa huscFv1E4 carries only one antigen binding site, inhibition of *C. burnetii* with 1E4, Fab 1E4, muscFv1E4 or huscFv1E4 was performed by incubating $1 \times 10^7$ virulent *C. burnetii* NMI with 300 μg of 1E4, 200 μg of Fab 1E4, 100 μg of muscFv1E4 or 100 μg of huscFv1E4 (which contained the same antigen binding sites) at 4° C. overnight. Six week-old BALB/c mice were infected by i.p. injection with $1 \times 10^7$ of 1E4, Fab1E4, muscFv1E4 or huscFv1E4 treated *C. burnetii*. The respective abilities of 1E4, Fab1E4, muscFv1E4 or huscFv1E4 to inhibit *C. burnetii* infection in BALB/c mice were evaluated by comparing splenomegaly, bacterial burden and histopathological changes in the spleen at 14 days post infection with PBS and mouse IgG2a isotype control.

Figure 16A:
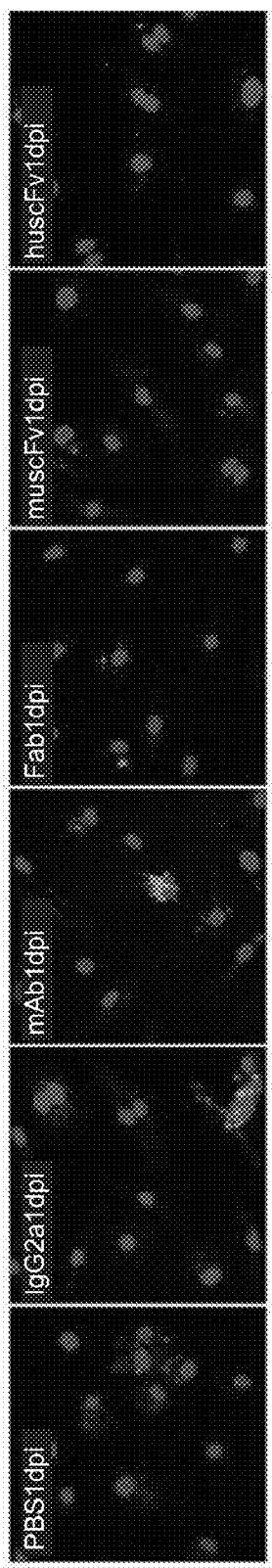
FIG. 16(A) evaluates the ability of 1E4, Fab1E4, muscFv1E4 and huscFv1E4 to inhibit *C. burnetii* infection in mouse BMDM.
Figure 16B:
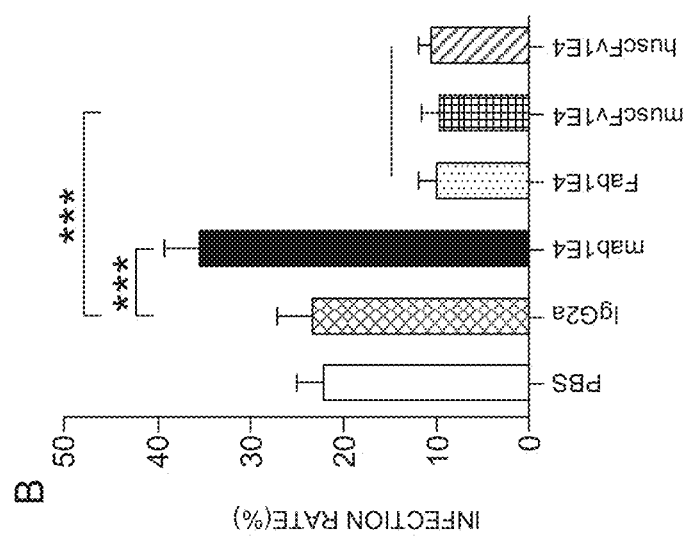
FIG. 16(B) evaluates the ability of 1E4, Fab1E4, muscFv1E4 and huscFv1E4 to inhibit *C. burnetii* infection in mouse BMDM.
Figure 16C:
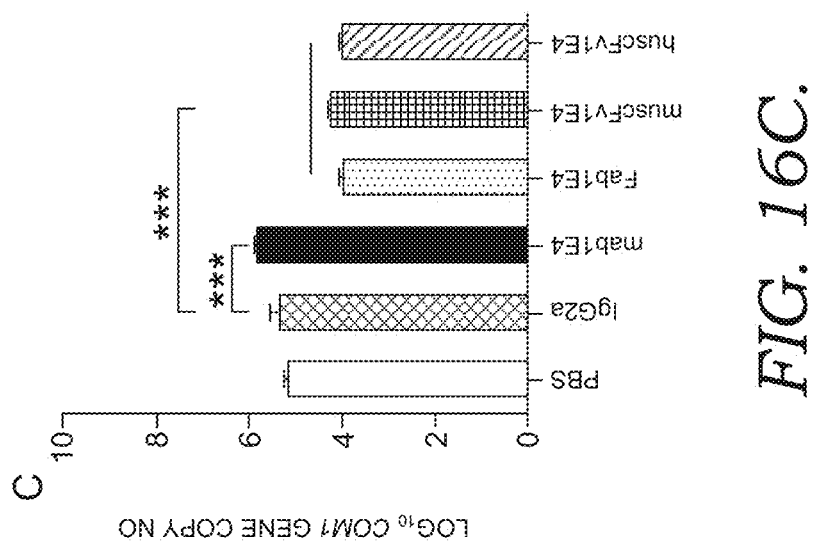
FIG. 16(C) evaluates the ability of 1E4, Fab1E4, muscFv1E4 and huscFv1E4 to inhibit *C. burnetii* infection in mouse BMDM.

To determine whether 1E4, Fab1E4, muscFv1E4 and huscFv1E4 can block *C. burnetii* infection in vitro, we examined if treatment of *C. burnetii* with 1E4, Fab1E4, muscFv1E4 or huscFv1E4 could inhibit *C. burnetii* infection in Bone Marrow-Derived Macrophages (BMDM). Bone marrow precursor cells were counted and placed into a culture flask in RPMI 1640 medium containing 10% fetal bovine serum and 30% of L929 cell conditioned medium (LCCM) at a concentration of $2 \times 10^6$ cells/ml and incubated at 37° C. for 7 days. Human monocyte-like (THP-1) cells (TIB-202; ATCC) were maintained in RPMI 1640 medium (INVITROGEN, Carlsbad, Calif.) supplemented with 10% fetal calf serum (HYCLONE, Logan, Utah) at 37° C. in 5% $CO_2$. THP-1 cells were differentiated into adherent, macrophage-like cells by treating freshly plated cells with PMA (200 nM; EMD Biosciences, San Diego, Calif.) for 3 days. For in vitro assay, BMDM or THP-1 derived human macrophages were removed from the substrate by HyQTase (HYCLONE) digestion and added to glass coverslips inserted in 24-well tissue culture dishes at a density of $2 \times 10^5$ per well. Compared to macrophages infected with PBS or IgG2a isotype control treated *C. burnetii*, fewer *C. burnetii* infected macrophages were observed in macrophages infected with Fab1E4, muscFv1E4 or huscFv1E4 treated *C. burnetii* while more *C. burnetii* infected macrophages were observed in macrophages infected with 1E4 treated *C. burnetii* (FIG. 16(A)). As shown in FIG. 16(B), compared to macrophages infected with PBS or IgG2a isotype control treated *C. burnetii*, the infection rate was significantly (P<0.001) decreased in macrophages infected with Fab1E4, muscFv1E4 or huscFv1E4 treated *C. burnetii* but it was significantly (P<0.001) increased in macrophages infected with 1E4 treated *C. burnetii* at 1 day post infection. In addition, *C. burnetii* genome copies in *C. burnetii* infected macrophages were measured by real-time-PCR at 1 day post infection. As shown in FIG. 16(C), compared to macrophages infected with PBS or IgG2a isotype control treated *C. burnetii*, the *C. burnetii* genome copies were significantly (P<0.001) lower in macrophages infected with Fab1E4, muscFv1E4 or huscFv1E4 treated *C. burnetii* but were significantly (P<0.01) higher in macrophages infected with 1E4 treated *C. burnetii*. Interestingly, there was no significant difference in *C. burnetii* infection rate and genome copies among macrophages infected with Fab 1E4, muscFv1E4 and huscFv1E4 treated *C. burnetii*. These results indicate that Fab1E4, muscFv1E4 and huscFv1E4 can block *C. burnetii* infection in vitro though their parent mAb 1E4 did not. The observation that *C. burnetii* infection rate and genome copies in macrophages infected with 1E4 treated *C. burnetii* were significantly higher than macrophages infected with PBS or IgG2a isotype control treated *C. burnetii* suggests that macrophages were able to uptake Ab-*C. burnetii* immune complex via Fc receptor-mediated phagocytosis.

*C. burnetii* inhibition assay in vitro: BMDM were used to examine if treatment of *C. burnetii* with 1E4, Fab1E4, muscFv1E4 or huscFv1E4 can inhibit *C. burnetii* infection in vitro. *C. burnetii* NMI was treated with 1E4, Fab 1E4, muscFv1E4 or huscFv1E4 in the same manner as described above and inoculated with macrophages at MOI of 100 and incubated at 37° C. for 2 h. After three times gentle washing with warm media to remove free bacteria, infected macrophages were cultured at 37° C. for 24 h. *C. burnetii* infection rate was determined at 24 h post infection by indirect IFA and the *C. burnetii* genomic copy numbers in macrophages were measured by Quantitative real time PCR assay. In addition, THP-1 derived human macrophages were used to determine whether huscFv1E4 can neutralize *C. burnetii* to block *C. burnetii* infection in human cells. *C. burnetii* treatment with huscFv1E4 and inoculation of human macrophages were performed in a similar manner as described in mouse macrophages.

Figure 17A:
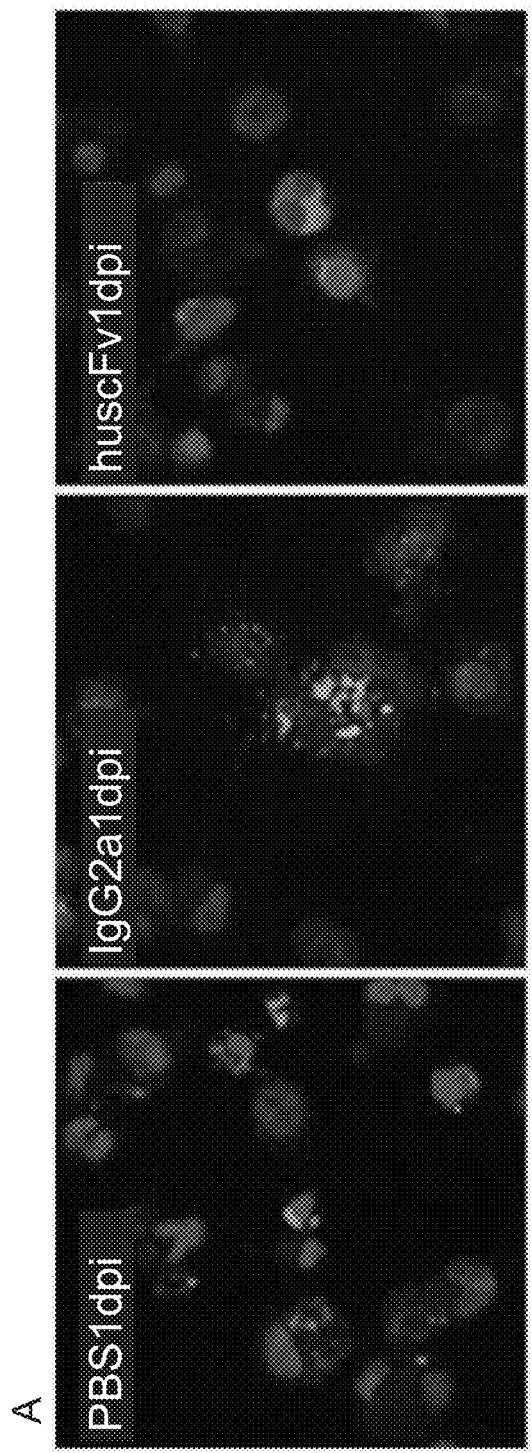
FIG. 17(A) evaluates the ability of huscFv1E4 to inhibit *C. burnetii* infection in human macrophages.
Figure 17B:
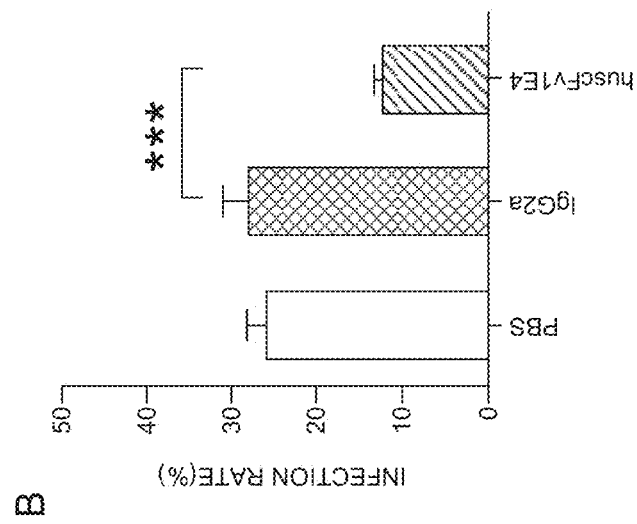
FIG. 17(B) evaluates the ability of huscFv1E4 to inhibit *C. burnetii* infection in human macrophages.
Figure 17C:
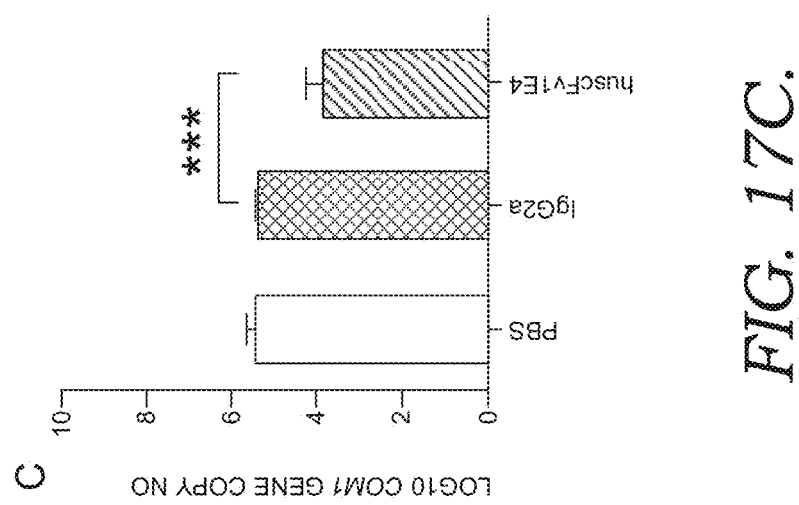
FIG. 17(C) evaluates the ability of huscFv1E4 to inhibit *C. burnetii* infection in human macrophages.

To determine whether huscFv1E4 can neutralize *C. burnetii* to block *C. burnetii* infection in human cells, THP-1 cell derived human macrophages were infected with PBS, IgG2a isotype control or huscFv1E4 treated *C. burnetii*. As shown in FIG. 17(A), compared to human macrophages infected with PBS or IgG2a isotype control treated *C. burnetii*, fewer *C. burnetii* infected macrophages were observed in macrophages infected with huscFv1E4 treated *C. burnetii* at 1 day post infection. In addition, the *C. burnetii* infection rate and genome copies in human macrophages infected with huscFv1E4 treated *C. burnetii* were significantly ($P<0.001$) lower than macrophages infected with PBS or IgG2a isotype control treated *C. burnetii* (FIGS. 17(B) & (C)). These results demonstrate that huscFv1E4 was able to neutralize *C. burnetii* to block *C. burnetii* infection in human cells and suggest that huscFv1E4 can be used to prevent human Q fever.

To determine whether 1E4, Fab1E4, muscFv1E4 and huscFv1E4 can directly kill *C. burnetii*, viable and nonviable bacteria in 1E4, Fab1E4, muscFv1E4 or huscFv1E4 treated *C. burnetii* were stained with BacLight kit and analyzed by fluorescence microscopy. In this assay, bacteria were stained with a green fluorescent dye (SYTO9) and a red fluorescent dye (PI). Since SYTO9 can penetrate all bacterial cells but PI only penetrates membrane damaged bacteria, viable bacteria will be stained by SYTO9 as green color while dead bacteria will be stained by PI as red color. More viable bacteria (green) were observed in 1E4 treated *C. burnetii* but more dead bacteria were found in EDTA treated *C. burnetii* (data not shown). Compared to PBS or IgG2a isotype control treated *C. burnetii*, a similar number of dead bacteria was found in 1E4, Fab1E4, muscFv1E4 or huscFv1E4 treated *C. burnetii* but significantly higher numbers of dead bacteria ($p<0.001$) were observed in EDTA treated *C. burnetii*. These results suggest that neither 1E4 nor Fab1E4, muscFv1E4 and huscFv1E4 can mediate direct killing of virulent *C. burnetii*.

Fluorescence microscopic assay of viable and nonviable *C. burnetii* cells: Approximately $1 \times 10^7$ virulent *C. burnetii* PI organisms were incubated with 1E4, Fab1E4, muscFv1E4 or huscFv1E4 in the same manner as described above or IgG2a isotype control in 500 ul PBS at 4° C. overnight. In addition, *C. burnetii* treated with 10 mM EDTA at 4° C. for 1 h was used as positive controls. *C. burnetii* was pelleted at 15,000 rpm/min in a microfuge for 30 min, washed and resuspended in sterile 0.85% NaCl. The BacLight stock solution A (SYTO9) and B (PI) (INVITROGEN) were added and incubated in the dark at room temperature for 15 min according to the manufacturer's instructions. The stained solution was mounted in BacLight mounting oil (INVITROGEN) on a clear glass slide. A total of 100 PI organisms were counted per slide at 1,000× using a fluorescence microscope and the duplicate numbers of dead bacteria (stained red) were recorded.

Histopathology: Lungs and spleens were collected from mice at 14 days post challenge with *C. burnetii*, fixed in 10% formalin-PBS at least for 48 h, prepared as 5-μm paraffin-embedded sections by standard methods, and then sliced. Slides were stained with hematoxylin and eosin and examined in a blinded fashion for evaluation of histopathology.

Statistical analysis: Statistical comparisons were performed with Prism 5.0 (GRAPHPAD SOFTWARE INC. San Diego, Calif.). Results expressed as means±standard deviations were compared with the two-sample Student's t-test or one-way ANOVA and the post test. Differences were considered significant at $p<0.05$.

In one embodiment, there is a composition for protection against *C. burnetti* infection in a subject comprising monoclonal antibodies 1E4, muscFv1E4 or huscFv1E4. In another embodiment, the monoclonal antibodies muscFv1E4 and huscFv1E4 comprise a polypeptide sequence of SEQ ID NO: 5 and SEQ ID NO: 6, respectively, or a polypeptide sequence having at least 90% identity to SEQ ID NO: 5 and SEQ ID NO: 6. In another embodiment, the monoclonal antibodies muscFv1E4 and huscFv1E4 are capable of binding to m1E41920. In one embodiment, the monoclonal antibodies muscFv1E4 and huscFv1E4 are capable of binding to live *C. burnetii*. In one embodiment, the monoclonal antibodies muscFv1E4 and huscFv1E4 are capable of inhibiting *C. burnetii* infection of cell culture in vitro. In another embodiment, the monoclonal antibodies huscFv1E4 can inhibit *C. burnetii* infection of human macrophages in vitro. In one embodiment, the monoclonal antibodies huscFv1E4 can inhibit *C. burnetii* infection of human macrophages in vivo.

Despite *C. burnetii* being an obligate intracellular pathogen, previous studies have shown that passive transfer of Abs was able to confer significant protection against *C. burnetii* intraperitoneal infection in mice, demonstrating the possibility of development of Ab-based immunotherapeutic strategies to prevent human Q fever. Since passive administration of Abs can provide immediate immunity against biological agents and there is no licensed vaccine available for protection of Q fever in the US, development of Ab-based immunotherapeutic strategies to prevent human Q fever has a high potential impact for public health and biodefense against *C. burnetii* natural infection and the use of *C. burnetii* for biological warfare. Our recent study demonstrated that treatment of *C. burnetii* with the PI-LPS specific mAb 1E4 was able to inhibit *C. burnetii* infection in mice in a dose-dependent manner, suggesting that 1E4 is a protective mAb. However, it remains unknown whether passive administration of 1E4 will provide significant protection against *C. burnetii* natural infection. To prove the feasibility of using 1E4 to prevent *C. burnetii* natural infection, we examined if passive transfer of 1E4 would provide significant protection against *C. burnetii* aerosol challenge in SCID mice. The result indicated that passive transfer of 1E4 was able to confer significant protection against aerosolized *C. burnetii* in SCID mice. Since SCID mice lack functional B and T cells which may mimic chronic Q fever patients with immunocompromised conditions, this finding suggests that 1E4 may be useful to protect individuals with immunocompromised conditions against *C. burnetii* natural infection. To our knowledge, this is the first evidence demonstrating that passive transfer of Abs can provide protection against *C. burnetii* natural infection. Since *C. burnetii* infection in individuals with immunocompromised conditions can develop into more severe and fatal chronic diseases and there is no licensed vaccine available for protection of Q fever in the US, developing a humanized antibody to use as a prophylactic agent is important for protection of individuals at high risk of exposure from developing chronic Q fever.

One early study demonstrated that purified human anti-PI IgM was able to suppress *C. burnetii* replication in the mouse spleen when mixed with a suspension of organisms prior to inoculation of mice. In addition, our recent studies have shown that treatment of *C. burnetii* with 1E4 or purified IgM or IgG from formalin-inactivated PI vaccine immunized mouse sera was able to inhibit *C. burnetii* infection in BALB/c mice. This data suggests that anti-PI Abs may be able to inhibit *C. burnetii* infection via their ability to neutralize or kill the organisms. However, there has been no direct evidence to support this hypothesis. To address this question, we isolated the Fab fragment of 1E4 (Fab1E4) and examined if Fab 1E4 binding with *C. burnetii* would block *C. burnetii* infection in both in vitro and in vivo systems. The results indicated that Fab1E4 retained a binding capability comparable to 1E4 and was able to neutralize virulent *C. burnetii* resulting in inhibiting *C. burnetii* infection in both in vitro and in vivo systems. These observations provided clear evidence to support that anti-PI Abs are able to inhibit *C. burnetii* infection via their ability to neutralize the organisms. It has been shown that LPS was involved in the virulent *C. burnetii* NMI uptake by either mouse or human macrophages through binding to integrin and/or TLR4 receptors (26). Since *C. burnetii* is smaller (0.2-2 µm) than typical gram-negative bacteria (1-10 µm) and LPS covers most of the surface of NMI, it is possible that NMI cells might be easily occupied and coated by LPS specific antibodies. As 1E4 specifically recognizes PI-LPS, our results suggest that Fab1E4-mediated inhibition of *C. burnetii* infection might be due to its ability to bind with PI-LPS thereby blocking *C. burnetii* infection in susceptible host cells. In addition, we also investigated whether Ab binding with virulent *C. burnetii* can mediate direct killing of bacteria. The results suggest that Ab was unable to mediate direct killing of virulent *C. burnetii*. These findings provide direct evidence to demonstrate that anti-PI Abs mediated inhibition of *C. burnetii* infection is dependent on their ability to neutralize the organisms to block the infection but not dependent on their ability to directly kill bacteria.

The classic concept in our understanding of Ab structure and function is that the variable region determines the antigen binding, whereas the Fc segment determines the isotype, pharmacological characteristics and interaction with Fc receptors. The best documented direct effect of the variable region is virus neutralization, which is defined as the abrogation of virus infectivity by inhibiting virus attachment and early entry into susceptible host cells. In contrast, only a few studies have reported that the ability of Abs to block receptors is required for the uptake of intracellular bacterial pathogens and thereby inhibiting bacterial infection. In the present study, to determine the role of the variable region and Fc segment in 1E4 mediated passive protection, we examined if the variable region of 1E4 (Fab1E4) retains the ability of 1E4 to inhibit *C. burnetii* infection in both in vitro and in vivo systems. The in vivo *C. burnetii* inhibition experiment demonstrated that Fab1E4 was able to inhibit *C. burnetii* infection in mice but its ability to inhibit *C. burnetii* infection was lower than 1E4, suggesting that both the variable region and Fc segment may contribute to 1E4 mediated passive protection. The in vitro *C. burnetii* inhibition experiment indicated that compared to macrophages infected with PBS or IgG2a isotype control treated *C. burnetii*, the infection rate and genome copies were significantly decreased in macrophages infected with Fab1E4 treated *C. burnetii* but they were significantly increased in macrophages infected with 1E4 treated *C. burnetii*, suggesting that Fab1E4 inhibited *C. burnetii* infection in vitro but 1E4 did not. Thus, the results regarding Fab1E4 mediated protection from the in vitro experiment correlated to the results from the in vivo experiment and support that Fab1E4 was able to significantly inhibit *C. burnetii* infection. However, the results regarding 1E4 mediated protection from the in vitro experiment do not support that 1E4 had a higher ability than Fab1E4 to inhibit *C. burnetii* infection in mice. The observation that the infection rate and genome copies were significantly increased in macrophages infected with 1E4 treated *C. burnetii* correlated with several previous in vitro studies, suggesting that anti-*C. burnetii* specific Abs can increase the ability of phagocytes to uptake Ab-opsonized *C. burnetii*. This result can be explained by the possibility that 1E4-opsonized *C. burnetii* may enhance phagocytic activity of macrophages via Fc receptor-mediated effects resulting in the increased infection rate and genome copies in macrophages. In addition, the conflicting results regarding 1E4 mediated protection between in vivo and in vitro model systems may be due to the in vitro *C. burnetii* inhibition assay's inability to mimic the in vivo situation and it is difficult to use a cell culture system to rule out what happened after macrophages uptake Ab-opsonized *C. burnetii* in mice. Future studies to determine whether 1E4 and Fab1E4 treated *C. burnetii* can differentially stimulate immune response in mice and/or activate macrophages would be helpful to further understand the mechanisms of 1E4-mediated protective immunity against *C. burnetii* infection.

As we know, passive administration of mouse mAbs to humans is not safe because it can induce human anti-mouse Ab responses. Thus, although our results demonstrated that passive transfer of 1E4 can provide significant protection against *C. burnetii* natural infection in mice, 1E4 cannot be directly used to prevent Q fever in humans or treat Q fever patients. To further demonstrate the feasibility of using humanized 1E4 to prevent human Q fever, we generated an recombinant humanized Fab fragment of 1E4 (huscFv1E4) and examined if huscFv1E4 retains the ability of 1E4 to inhibit *C. burnetii* infection in mice and mouse macrophages. The results indicated that treatment of *C. burnetii* with huscFv1E4 significantly inhibited the *C. burnetii* infection in both in vitro and in vivo systems and there was no significant difference between huscFv1E4 and Fab1E4 in their ability to inhibit *C. burnetii* infection. In addition, our results also demonstrated that huscFv1E4 was able to neutralize *C. burnetii* to block *C. burnetii* infection in human macrophages. These results suggest that huscFv1E4 may be useful for preventing human Q fever. However, the observation that huscFv1E4 had lower inhibition capability than 1E4 in mice suggests that Fc segment may be required for 1E4-mediated complete passive protection. These data demonstrate that CDR grafting humanization retained comparable levels of protective ability of mouse mAb in both in vitro and in vivo systems and prove the feasibility of the generation of a fully humanized mAb 1E4 for preventing human Q fever.

It will be apparent to those skilled in the art that various modifications and variations can be made in the practice of the present method and in construction and use of the present technology departing from the scope or spirit of the invention. Other embodiments of the invention will be apparent to those skilled in the art from consideration of the specification and practice of the invention. It is intended that the specification and examples be considered as exemplary only.

What is claimed:

1. A lipopolysaccharide-based peptide mimetic for protection against infection of gram negative intracellular bacteria in a subject; wherein the lipopolysaccharide-based peptide mimetic sequence comprises a sequence of SLTWHKHELHRK (SEQ ID NO: 7) or SPPWHKHELHRK (SEQ ID NO: 8), or a peptide sequence having at least 90% identity to SLTWHKHELHRK (SEQ ID NO: 7) or SPPWHKHELHRK (SEQ ID NO: 8), or a pharmaceutically acceptable salt thereof.

2. The lipopolysaccharide-based peptide mimetic of claim 1, wherein the lipopolysaccharide-based peptide mimetic sequence is conjugated to keyhole limpet hemocyanin (KLH).

3. The lipopolysaccharide-based peptide mimetic of claim 1, wherein the lipopolysaccharide-based peptide mimetic sequence binds to a monoclonal antibody 1E4, muscFv1E4 or huscFv1E4.

4. The lipopolysaccharide-based peptide mimetic of claim 1, wherein the lipopolysaccharide-based peptide mimetic sequence comprises a WHXH motif, wherein X represents any amino acid.

5. A lipopolysaccharide-based peptide mimetic for protection against infection of gram negative intracellular bacteria in a subject, wherein the lipopolysaccharide-based peptide mimetic sequence comprises an amino acid sequence selected from the group consisting of:

1) SWFHPQRRHSHQ, (SEQ ID NO: 9)
2) SWMPHPRWSPQH, (SEQ ID NO: 10)
3) MHRAPSTHKLLP, (SEQ ID NO: 11)
4) ASWHQHYMKHKP, (SEQ ID NO: 12)
5) SEFHRHGDKEHK, (SEQ ID NO: 13)
6) CEFPRSWDMETN, (SEQ ID NO: 14)
7) SLTRHKPEPHRK, (SEQ ID NO: 15)
8) GGWHKHISRSDP, (SEQ ID NO: 16)
9) YHKHPHTYHNFK, (SEQ ID NO: 17)
10) HPKHPHTHTNDQ, (SEQ ID NO: 18)
11) HMHMHQHVAQTQ, (SEQ ID NO: 19)
12) HMGMTKINYSAL, (SEQ ID NO: 20)
13) SNYSDVKRLPTV, (SEQ ID NO: 21) and
14) SVNWQKQTISNL, (SEQ ID NO: 22)

or a pharmaceutically acceptable salt thereof.

6. The lipopolysaccharide-based peptide mimetic of claim 5, wherein the lipopolysaccharide-based peptide mimetic sequence is conjugated to keyhole limpet hemocyanin (KLH).

7. The lipopolysaccharide-based peptide mimetic of claim 5, wherein the lipopolysaccharide-based peptide mimetic sequence binds to a monoclonal antibody 1E4, muscFv1E4 or huscFv1E4.

* * * * *

SEQUENCE LISTING

<160> NUMBER OF SEQ ID NOS: 22

<210> SEQ ID NO 1
<211> LENGTH: 137
<212> TYPE: PRT

```
<213> ORGANISM: Mus musculus
<220> FEATURE:
<221> NAME/KEY: misc_feature
<222> LOCATION: (133)..(133)
<223> OTHER INFORMATION: Xaa can be any naturally occurring amino acid

<400> SEQUENCE: 1

Glu Cys Gln Leu Glu Ser Gly Gly Gly Leu Val Arg Pro Gly Asn
1               5                   10                  15

Ser Leu Lys Leu Ser Cys Val Thr Ser Gly Phe Thr Phe Ser Asn Tyr
                20                  25                  30

Arg Val His Trp Leu Arg Gln Pro Pro Gly Lys Arg Leu Glu Trp Ile
                35                  40                  45

Ala Val Ile Ala Val Lys Ser Asp Asn Tyr Gly Ala Asn Tyr Ala Glu
            50                  55                  60

Ser Val Lys Gly Arg Phe Thr Ile Ser Arg Asp Asp Ser Lys Ser Ser
65                  70                  75                  80

Val Tyr Leu Gln Met Asn Arg Leu Arg Glu Glu Asp Thr Ala Thr Tyr
                85                  90                  95

Tyr Cys Arg Ser Thr Val Val Val Met Gly Asp Tyr Phe Ala Met Asp
                100                 105                 110

Tyr Trp Gly Gln Gly Thr Ser Val Thr Val Ser Ser Ala Lys Thr Thr
                115                 120                 125

Ala Pro Ser Val Xaa Pro Leu Ala Pro
            130                 135

<210> SEQ ID NO 2
<211> LENGTH: 100
<212> TYPE: PRT
<213> ORGANISM: Mus musculus

<400> SEQUENCE: 2

Asp Ile Glu Leu Thr Gln Ser Pro Ala Ile Leu Ser Val Ser Pro Gly
1               5                   10                  15

Glu Arg Val Ser Phe Ser Cys Arg Ala Ser Gln Asn Ile Gly Thr Tyr
                20                  25                  30

Ile His Trp Tyr Gln Gln Arg Thr Asn Gly Ser Pro Arg Leu Leu Ile
                35                  40                  45

Lys Tyr Ala Ser Glu Ser Val Ser Gly Ile Pro Ser Arg Phe Ser Gly
            50                  55                  60

Arg Gly Ser Gly Thr Asp Phe Thr Leu Ser Ile Ser Ser Val Glu Ser
65                  70                  75                  80

Glu Asp Ile Ala Asp Tyr Tyr Cys Gln Gln Ser Asn Thr Trp Pro Tyr
                85                  90                  95

Thr Phe Gly Gly
                100

<210> SEQ ID NO 3
<211> LENGTH: 412
<212> TYPE: DNA
<213> ORGANISM: Mus musculus

<400> SEQUENCE: 3
tgaatgtcag ctcgaggagt ctgggggagg cttggtgagg cctggaaatt ctctgaaact    60
ctcctgtgtt acctcgggat tcactttcag taactaccgg gtgcactggc ttcgccagcc   120
tccagggaag aggctggagt ggattgctgt aattgcagtc aaatctgata attatggagc   180
aaattatgca gagtctgtga aaggcagatt cactatttca agagatgatt caaaaagcag   240
```

```
tgtctacctg cagatgaaca gattaagaga ggaagacact gccacttatt attgccgatc    300
tacggtagtt gttatgggag attactttgc tatggactac tggggtcaag gaacctcagt    360
caccgtctcc tcagccaaaa caacagcccc atcggtcttc cactggcccc tg            412
```

<210> SEQ ID NO 4
<211> LENGTH: 300
<212> TYPE: DNA
<213> ORGANISM: Mus musculus

<400> SEQUENCE: 4

```
gacattgagc tcacccagtc tccagccatc ctgtctgtga gtccaggaga aagagtcagt    60
ttctcctgta gggccagtca gaacattggc acatacatac actggtatca gcaaagaaca    120
aatggttctc caaggcttct cataaagtat gcttctgagt ctgtctctgg gatcccttcc    180
aggtttagtg gcagaggatc aggacagat tttactctta gcatcagcag tgtggagtct    240
gaagatattg cagattatta ctgtcaacaa agtaatacct ggccgtacac gttcggaggg    300
```

<210> SEQ ID NO 5
<211> LENGTH: 289
<212> TYPE: PRT
<213> ORGANISM: Mus musculus

<400> SEQUENCE: 5

```
Met Lys Tyr Leu Leu Pro Thr Ala Ala Ala Gly Leu Leu Leu Leu Ala
1               5                   10                  15

Ala Gln Pro Ala Met Ala Glu Cys Leu Glu Glu Ser Gly Gly Gly Leu
            20                  25                  30

Val Arg Pro Gly Asn Ser Leu Lys Leu Ser Cys Val Thr Ser Gly Phe
        35                  40                  45

Thr Phe Ser Asn Tyr Arg Val His Trp Leu Arg Gln Pro Pro Gly Lys
    50                  55                  60

Arg Leu Glu Trp Ile Ala Val Ile Ala Val Lys Ser Asp Asn Tyr Gly
65                  70                  75                  80

Ala Asn Tyr Ala Glu Ser Val Lys Gly Arg Phe Thr Ile Ser Arg Asp
                85                  90                  95

Asp Ser Lys Ser Ser Val Tyr Leu Gln Met Asn Arg Leu Arg Glu Glu
            100                 105                 110

Asp Thr Ala Thr Tyr Tyr Cys Arg Ser Thr Val Val Met Gly Asp
        115                 120                 125

Tyr Phe Ala Met Asp Tyr Trp Gly Gln Gly Thr Ser Val Thr Val Ser
    130                 135                 140

Ser Gly Gly Gly Gly Ser Gly Gly Gly Gly Ser Gly Gly Gly Gly Ser
145                 150                 155                 160

Asp Ile Glu Leu Thr Gln Ser Pro Ala Ile Leu Ser Val Ser Pro Gly
                165                 170                 175

Glu Arg Val Ser Phe Ser Cys Arg Ala Ser Gln Asn Ile Gly Thr Tyr
            180                 185                 190

Ile His Trp Tyr Gln Gln Arg Thr Asn Gly Ser Pro Arg Leu Leu Ile
        195                 200                 205

Lys Tyr Ala Ser Glu Ser Val Ser Gly Ile Pro Ser Arg Phe Ser Gly
    210                 215                 220

Arg Gly Ser Gly Thr Asp Phe Thr Leu Ser Ile Ser Ser Val Glu Ser
225                 230                 235                 240

Glu Asp Ile Ala Asp Tyr Tyr Cys Gln Gln Ser Asn Thr Trp Pro Tyr
```

```
                        245                 250                 255
Thr Phe Gly Gly Gly Thr Lys Leu Glu Ile Lys Arg Ala Asp Ala Ala
                    260                 265                 270
Pro Thr Val Ser Lys Leu Ala Ala Ala Leu Glu His His His His His
                275                 280                 285
His

<210> SEQ ID NO 6
<211> LENGTH: 289
<212> TYPE: PRT
<213> ORGANISM: Homo sapiens

<400> SEQUENCE: 6

Met Lys Tyr Leu Leu Pro Thr Ala Ala Ala Gly Leu Leu Leu Leu Ala
1               5                   10                  15
Ala Gln Pro Ala Met Ala Gln Cys Leu Val Glu Ser Gly Gly Gly Val
                20                  25                  30
Val Gln Pro Gly Arg Ser Leu Arg Leu Ser Cys Ala Ala Ser Gly Phe
            35                  40                  45
Thr Phe Ser Asn Tyr Arg Val His Trp Val Arg Gln Ala Pro Gly Lys
        50                  55                  60
Gly Leu Glu Trp Ile Ala Val Ile Ala Val Lys Ser Asp Asn Tyr Gly
65                  70                  75                  80
Ala Asn Tyr Ala Glu Ser Val Lys Gly Arg Phe Thr Ile Ser Arg Asp
                85                  90                  95
Asn Ser Lys Asn Thr Leu Tyr Leu Gln Met Asn Ser Leu Arg Ala Glu
                100                 105                 110
Asp Thr Ala Val Tyr Tyr Cys Arg Ser Thr Val Val Met Gly Asp
            115                 120                 125
Tyr Phe Ala Met Asp Tyr Trp Gly Gln Gly Thr Ser Val Thr Val Ser
        130                 135                 140
Ser Gly Gly Gly Gly Ser Gly Gly Gly Ser Gly Gly Gly Gly Ser
145                 150                 155                 160
Asp Ile Val Leu Thr Gln Ser Pro Ala Phe Leu Ser Val Thr Pro Gly
                165                 170                 175
Glu Lys Val Thr Ile Thr Cys Arg Ala Ser Gln Asn Ile Gly Thr Tyr
                180                 185                 190
Ile His Trp Tyr Gln Gln Lys Pro Asp Gln Ala Pro Lys Leu Leu Ile
            195                 200                 205
Lys Tyr Ala Ser Glu Ser Val Ser Gly Val Pro Ser Arg Phe Ser Gly
        210                 215                 220
Ser Gly Ser Gly Thr Asp Phe Thr Phe Thr Ile Ser Ser Leu Glu Ala
225                 230                 235                 240
Glu Asp Ala Ala Thr Tyr Tyr Cys Gln Gln Ser Asn Thr Trp Pro Tyr
                245                 250                 255
Thr Phe Gly Gly Gly Thr Lys Leu Glu Ile Lys Arg Ala Asp Ala Ala
                    260                 265                 270
Pro Thr Val Ser Lys Leu Ala Ala Ala Leu Glu His His His His His
                275                 280                 285
His

<210> SEQ ID NO 7
<211> LENGTH: 12
<212> TYPE: PRT
<213> ORGANISM: Artificial Sequence
```

```
<220> FEATURE:
<223> OTHER INFORMATION: Peptide Phage Display Library (Ph.D.TM -12
      Phage Display Peptide Library from NEB)

<400> SEQUENCE: 7

Ser Leu Thr Trp His Lys His Glu Leu His Arg Lys
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Peptide Phage Display Library (Ph.D.TM -12
      Phage Display Peptide Library from NEB)

<400> SEQUENCE: 8

Ser Pro Pro Trp His Lys His Glu Leu His Arg Lys
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Peptide Phage Display Library (Ph.D.TM -12
      Phage Display Peptide Library from NEB)

<400> SEQUENCE: 9

Ser Trp Phe His Pro Gln Arg Arg His Ser His Gln
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Peptide Phage Display Library (Ph.D.TM -12
      Phage Display Peptide Library from NEB)

<400> SEQUENCE: 10

Ser Trp Met Pro His Pro Arg Trp Ser Pro Gln His
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Peptide Phage Display Library (Ph.D.TM -12
      Phage Display Peptide Library from NEB)

<400> SEQUENCE: 11

Met His Arg Ala Pro Ser Thr His Lys Leu Leu Pro
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Peptide Phage Display Library (Ph.D.TM -12
      Phage Display Peptide Library from NEB)

<400> SEQUENCE: 12

Ala Ser Trp His Gln His Tyr Met Lys His Lys Pro
1               5                   10
```

<210> SEQ ID NO 13
<211> LENGTH: 12
<212> TYPE: PRT
<213> ORGANISM: Artificial Sequence
<220> FEATURE:
<223> OTHER INFORMATION: Peptide Phage Display Library (Ph.D.TM -12
      Phage Display Peptide Library from NEB)

<400> SEQUENCE: 13

Ser Glu Phe His Arg His Gly Asp Lys Glu His Lys
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Peptide Phage Display Library (Ph.D.TM -12
      Phage Display Peptide Library from NEB)

<400> SEQUENCE: 14

Cys Glu Phe Pro Arg Ser Trp Asp Met Glu Thr Asn
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Peptide Phage Display Library (Ph.D.TM -12
      Phage Display Peptide Library from NEB)

<400> SEQUENCE: 15

Ser Leu Thr Arg His Lys Pro Glu Pro His Arg Lys
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Peptide Phage Display Library (Ph.D.TM -12
      Phage Display Peptide Library from NEB)

<400> SEQUENCE: 16

Gly Gly Trp His Lys His Ile Ser Arg Ser Asp Pro
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Peptide Phage Display Library (Ph.D.TM -12
      Phage Display Peptide Library from NEB)

<400> SEQUENCE: 17

Tyr His Lys His Pro His Thr Tyr His Asn Phe Lys
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Peptide Phage Display Library (Ph.D.TM -12
      Phage Display Peptide Library from NEB)

```
<400> SEQUENCE: 18

His Pro Lys His Pro His Thr His Thr Asn Asp Gln
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Peptide Phage Display Library (Ph.D.TM -12
      Phage Display Peptide Library from NEB)

<400> SEQUENCE: 19

His Met His Met His Gln His Val Ala Gln Thr Gln
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Peptide Phage Display Library (Ph.D.TM -12
      Phage Display Peptide Library from NEB)

<400> SEQUENCE: 20

His Met Gly Met Thr Lys Ile Asn Tyr Ser Ala Leu
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Peptide Phage Display Library (Ph.D.TM -12
      Phage Display Peptide Library from NEB)

<400> SEQUENCE: 21

Ser Asn Tyr Ser Asp Val Lys Arg Leu Pro Thr Val
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Peptide Phage Display Library (Ph.D.TM -12
      Phage Display Peptide Library from NEB)

<400> SEQUENCE: 22

Ser Val Asn Trp Gln Lys Gln Thr Ile Ser Asn Leu
1               5                   10
```